(12) United States Patent
Scarrott et al.

(10) Patent No.: US 7,568,481 B2
(45) Date of Patent: *Aug. 4, 2009

(54) INDICATING DEVICE

(75) Inventors: Peter Mycola Scarrott, London (CA); Jerry R. Grychowski, Lake Zurich, IL (US); James Nick Schmidt, London (CA); Martin P. Foley, London (CA)

(73) Assignee: Trudell Medical International, London (CA)

(*) Notice: Subject to any disclaimer, the term of this patent is extended or adjusted under 35 U.S.C. 154(b) by 374 days.

This patent is subject to a terminal disclaimer.

(21) Appl. No.: 11/136,044

(22) Filed: May 24, 2005

(65) Prior Publication Data

US 2005/0205512 A1 Sep. 22, 2005

Related U.S. Application Data

(63) Continuation of application No. 10/876,005, filed on Jun. 24, 2004, now Pat. No. 6,926,002, which is a continuation of application No. 10/409,247, filed on Apr. 8, 2003, now Pat. No. 6,953,039, which is a continuation of application No. 10/039,744, filed on Oct. 26, 2001, now Pat. No. 6,761,161, which is a continuation of application No. 09/303,043, filed on Apr. 30, 1999, now Pat. No. 6,336,453, and a continuation-in-part of application No. 09/603,427, filed on Jun. 26, 2000, now Pat. No. 6,328,037, which is a continuation of application No. 09/073,275, filed on May 5, 1998, now Pat. No. 6,082,358.

(51) Int. Cl.
*A62B 7/00* (2006.01)

(52) U.S. Cl. ............................. 128/205.23; 128/200.23

(58) Field of Classification Search ............ 128/200.14, 128/200.18, 200.23, 203.15, 203.12, 203.23, 128/205.23; 222/32, 36, 162; 116/307–309, 116/311–315, 317, 318
See application file for complete search history.

(56) References Cited

U.S. PATENT DOCUMENTS 165,054 A  6/1875  Baldwin (Continued)

FOREIGN PATENT DOCUMENTS

AU  598250 B2  6/1990

(Continued)

OTHER PUBLICATIONS

U.S. Department of Health and Human Services, Food and Drug Administration, Center for Drug Evaluation and Research (CDER)—Clinical, "Guidance for Industry: Integration of Dose-Counting Mechanisms into MDI Drug Products—Draft Guidance," dated Nov. 2001, 6 pages.

(Continued)

*Primary Examiner*—Steven O Douglas
(74) *Attorney, Agent, or Firm*—Brinks Hofer Gilson & Lione

(57) ABSTRACT

An indicating device for indicating the number of dosages of a substance that have been dispensed from or remain in a container includes a first indicator member incrementally moveable to a plurality of positions and a second indicator member operably connected to the first indicator member. The second indicator member is moveable in response to a predetermined number of movements of the first indicator member. One of the first and second indicator members includes numerical indicia and the other thereof includes color indicia.

25 Claims, 15 Drawing Sheets

U.S. PATENT DOCUMENTS

| | | |
|---|---|---|
| 498,851 A | 6/1893 | Jones |
| 1,219,858 A | 3/1917 | Patterson |
| 2,455,962 A | 12/1948 | Wheeler et al. |
| 2,580,292 A | 12/1951 | Geary et al. |
| 2,587,147 A | 2/1952 | Guion et al. |
| 2,630,027 A | 3/1953 | Wunderlich |
| 2,644,452 A | 7/1953 | Brown |
| 2,767,680 A | 10/1956 | Lermer |
| 2,770,711 A | 11/1956 | Baranowski |
| 2,841,190 A | 7/1958 | Scheck |
| 2,883,086 A | 4/1959 | Davison et al. |
| 2,939,597 A | 6/1960 | Greene |
| 2,943,730 A | 7/1960 | Tregilgas |
| 2,953,242 A | 9/1960 | Shaw |
| 3,001,524 A | 9/1961 | Maison et al. |
| 3,073,468 A | 1/1963 | Arneson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |
| 3,187,963 A | 6/1965 | Anderson |
| 3,189,232 A | 6/1965 | Joffe |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,361,306 A | 1/1968 | Grim |
| 3,402,863 A | 9/1968 | Green |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,568,629 A | 3/1971 | Porter |
| 3,572,282 A | 3/1971 | Trump et al. |
| 3,589,563 A | 6/1971 | Carragan et al. |
| 3,612,349 A | 10/1971 | Thomas |
| 3,654,890 A | 4/1972 | Rigney et al. |
| 3,655,952 A | 4/1972 | Johnson et al. |
| 3,688,945 A | 9/1972 | Harman, Jr. et al. |
| 3,753,417 A | 8/1973 | Garby |
| 3,757,732 A | 9/1973 | Frey |
| 3,766,882 A | 10/1973 | Babbitt, III |
| 3,789,843 A | 2/1974 | Armstrong et al. |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullett |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,950,939 A | 4/1976 | Meisner |
| 3,960,713 A | 6/1976 | Carey |
| 3,977,554 A | 8/1976 | Costa |
| 3,994,421 A | 11/1976 | Hansen |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,319,128 A | 3/1982 | Dow et al. |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| 4,749,093 A | 6/1988 | Trick |
| 4,753,189 A | 6/1988 | Mastman et al. |
| 4,756,423 A | 7/1988 | Holtsch |
| 4,782,966 A | 11/1988 | Thackrey |
| 4,792,664 A | 12/1988 | Schwab |
| 4,817,822 A | 4/1989 | Rand et al. |
| 4,890,572 A | 1/1990 | Huang |
| 4,896,855 A | 1/1990 | Furnish |
| 4,934,358 A | 6/1990 | Nilsson et al. |
| 4,934,568 A | 6/1990 | Fuchs |
| 4,947,875 A | 8/1990 | Brooks et al. |
| 4,955,371 A | 9/1990 | Zamba et al. |
| 4,969,578 A | 11/1990 | Gander et al. |
| 4,973,250 A | 11/1990 | Milman |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,806 A | 7/1991 | Zoltan et al. |
| 5,027,808 A | 7/1991 | Rich et al. |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |

| | | |
|---|---|---|
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,209,375 A | 5/1993 | Fuchs |
| 5,215,079 A | 6/1993 | Fine et al. |
| 5,217,004 A | 6/1993 | Blasnik et al. |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Ambrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |
| 5,349,944 A | 9/1994 | Chippendale et al. |
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,447,150 A | 9/1995 | Bacon |
| 5,448,042 A | 9/1995 | Robinson et al. |
| 5,482,030 A | 1/1996 | Klein |
| 5,482,163 A | 1/1996 | Hoffman |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,574,268 A | 11/1996 | Herman et al. |
| 5,577,335 A | 11/1996 | Tucker |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,657,748 A | 8/1997 | Braithwaite |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,720,392 A | 2/1998 | Price |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,826,571 A | 10/1998 | Casper et al. |
| 5,829,434 A | 11/1998 | Ambrosio et al. |
| 5,845,777 A | 12/1998 | Najmi |
| 5,852,590 A | 12/1998 | de la Huerga |
| 5,871,007 A | 2/1999 | Clark, Jr. |
| 5,873,995 A | 2/1999 | Huang et al. |
| 5,882,507 A | 3/1999 | Tanner et al. |
| 5,896,855 A | 4/1999 | Hobbs et al. |
| 5,896,990 A | 4/1999 | Barzana |
| 5,899,201 A | 5/1999 | Schultz et al. |
| 5,904,139 A | 5/1999 | Hauser |
| 5,957,896 A | 9/1999 | Bendek et al. |
| 5,979,698 A | 11/1999 | Deal |
| 5,988,496 A | 11/1999 | Bruna |
| 6,000,159 A | 12/1999 | Hornung |
| 6,003,467 A | 12/1999 | Shelton-Ferrell et al. |
| 6,012,450 A | 1/2000 | Rubsamen |
| 6,029,659 A | 2/2000 | O'Connor |
| 6,032,609 A | 3/2000 | Luoma |
| 6,059,133 A | 5/2000 | Lai |
| 6,062,214 A | 5/2000 | Howlett |
| 6,076,521 A | 6/2000 | Lindahl et al. |
| 6,082,358 A | 7/2000 | Scarrott et al. |
| 6,089,180 A | 7/2000 | Nichols, Jr. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo |
| 6,152,067 A | 11/2000 | Mathison |
| 6,155,251 A | 12/2000 | Hauser |
| 6,161,724 A | 12/2000 | Blacker et al. |
| 6,164,494 A | 12/2000 | Marelli |
| 6,186,364 B1 | 2/2001 | Dobbs |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,328,037 B1 | 12/2001 | Scarrott et al. |
| 6,336,453 B1 | 1/2002 | Scarrott et al. |
| 6,360,739 B1 | 3/2002 | Rand et al. |
| 6,405,727 B1 | 6/2002 | MacMichael et al. |
| 6,415,785 B1 | 7/2002 | Stage |
| 6,425,392 B1 | 7/2002 | Sosiak |
| 6,431,168 B1 | 8/2002 | Rand et al. |
| 6,435,372 B1 | 8/2002 | Blacker et al. |
| 6,446,627 B1 | 9/2002 | Bowman et al. |
| 6,474,331 B1 | 11/2002 | Rand et al. |
| 6,481,438 B1 | 11/2002 | Gallem et al. |
| 6,484,717 B1 | 11/2002 | Dagsland et al. |
| 6,516,799 B1 | 2/2003 | Greenwood et al. |
| 6,523,688 B1 | 2/2003 | Palmieri |
| 6,529,446 B1 * | 3/2003 | de la Huerga ................. 368/10 |
| 6,561,384 B2 | 5/2003 | Blacker et al. |
| 6,601,582 B2 | 8/2003 | Rand et al. |
| 6,615,827 B2 | 9/2003 | Greenwood et al. |
| 6,659,307 B1 | 12/2003 | Stradella |
| 6,679,251 B1 | 1/2004 | Gallem et al. |
| 6,701,917 B2 | 3/2004 | O'Leary |
| 6,718,972 B2 | 4/2004 | O'Leary |
| 6,729,330 B2 | 5/2004 | Scarrott et al. |
| 6,752,153 B1 | 6/2004 | Eckert |
| 6,761,161 B2 | 7/2004 | Scarrott et al. |
| 6,766,799 B2 | 7/2004 | Edwards et al. |
| 6,769,601 B2 | 8/2004 | Haikarainen et al. |
| 6,796,267 B2 | 9/2004 | DuBarry |
| 6,907,876 B1 | 6/2005 | Clark et al. |
| 6,926,002 B2 * | 8/2005 | Scarrott et al. ......... 128/200.14 |
| 7,004,164 B2 * | 2/2006 | Scarrott ................ 128/205.23 |
| 7,100,530 B2 * | 9/2006 | Lu ............................ 116/307 |
| 7,107,986 B2 | 9/2006 | Rand et al. |
| 7,137,391 B2 | 11/2006 | Bruna |
| 7,143,764 B1 | 12/2006 | Dagsland et al. |

| | | | | | | |
|---|---|---|---|---|---|---|
| 7,156,258 | B2 | 1/2007 | Eckert | EP | 1 369 139 A1 | 12/2003 |
| 7,191,918 | B2 | 3/2007 | Ouyang et al. | EP | 1 220 802 B1 | 2/2004 |
| 7,195,134 | B2 | 3/2007 | Ouyang et al. | FR | 2 743 055 A1 | 7/1997 |
| 2002/0000225 | A1 | 1/2002 | Schuler et al. | GB | 998148 | 7/1965 |
| 2002/0153005 | A1 | 10/2002 | Scarrott et al. | GB | 1058636 | 2/1967 |
| 2003/0183225 | A1 | 10/2003 | Knudsen | GB | 1 290 474 | 9/1972 |
| 2003/0200964 | A1 | 10/2003 | Blakley et al. | GB | 1 290 484 | 9/1972 |
| 2003/0209239 | A1 | 11/2003 | Rand et al. | GB | 1317315 | 5/1973 |
| 2003/0209964 | A1 | 11/2003 | Kang | GB | 2 036 695 A | 7/1980 |
| 2004/0065326 | A1 | 4/2004 | MacMichael et al. | GB | 2 063 075 A | 6/1981 |
| 2004/0069301 | A1 | 4/2004 | Bacon | GB | 2 092 991 A | 8/1982 |
| 2004/0094147 | A1 | 5/2004 | Schyra et al. | GB | 2 104 393 A | 3/1983 |
| 2004/0144798 | A1 | 7/2004 | Ouyang et al. | GB | 2 191 032 A | 12/1987 |
| 2004/0149772 | A1 | 8/2004 | Ouyang | GB | 2 195 544 A | 4/1988 |
| 2004/0149773 | A1 | 8/2004 | Ouyang et al. | GB | 2 348 928 A | 10/2000 |
| 2004/0221840 | A1 | 11/2004 | Stockman-Lamb | GB | 2 414 187 A | 11/2005 |
| 2004/0255935 | A1 | 12/2004 | Bruna | JP | 6-26891 | 4/1994 |
| 2004/0255936 | A1 | 12/2004 | Urbanus | WO | WO 86/02275 | 4/1986 |
| 2005/0011515 | A1 | 1/2005 | Lee et al. | WO | WO 87/04354 | 8/1987 |
| 2005/0056276 | A1 | 3/2005 | Schuler et al. | WO | WO 90/10470 | 9/1990 |
| 2005/0268905 | A1 | 12/2005 | Rasmussen et al. | WO | WO 91/06334 | 5/1991 |
| 2005/0284471 | A1 | 12/2005 | Bruna | WO | WO 92/07600 | 5/1992 |
| 2006/0254581 | A1 | 11/2006 | Genova et al. | WO | WO 92/09324 | 6/1992 |
| | | | | WO | WO 92/15353 | 9/1992 |
| | | FOREIGN PATENT DOCUMENTS | | WO | WO 92/17231 | 10/1992 |
| CA | | 535518 | 1/1957 | WO | WO 93/24167 | 12/1993 |
| CA | | 2 152 088 A | 7/1994 | WO | WO 94/11272 | 5/1994 |
| CA | | 2 181 789 C | 6/1996 | WO | WO 94/14492 | 7/1994 |
| CA | | 2 486 892 A1 | 12/1998 | WO | WO 95/34874 | 12/1995 |
| CA | | 2 315 777 A1 | 7/1999 | WO | WO 96/16686 | 6/1996 |
| CA | | 2 331 179 A1 | 11/1999 | WO | WO 96/16687 | 6/1996 |
| CA | | 2 383 425 A1 | 3/2001 | WO | WO 96/39337 | 12/1996 |
| CA | | 2 388 958 A1 | 3/2001 | WO | WO 98/01822 | 1/1998 |
| CA | | 2 414 118 A1 | 1/2002 | WO | WO 98/56444 | 12/1998 |
| CA | | 2 420 171 A1 | 3/2002 | WO | WO 98/56445 | 12/1998 |
| DE | | 6 603 758 | 7/1969 | WO | WO 99/36115 | 7/1999 |
| DE | | 27 02 539 A1 | 1/1977 | WO | WO 99/57019 | 11/1999 |
| DE | | 3336486 A1 | 4/1984 | WO | WO 00/09187 | 2/2000 |
| DE | | G 8 590 143.1 | 10/1985 | WO | WO 00/59806 | 10/2000 |
| DE | | G 86 02 238.5 | 5/1986 | WO | WO 01/28887 A1 | 4/2001 |
| EP | | 0 028 929 A2 | 5/1981 | WO | WO 01/29765 | 4/2001 |
| EP | | 0 288 929 A2 | 5/1981 | WO | WO 01/37909 A1 | 5/2001 |
| EP | | 0 098 939 A2 | 1/1984 | WO | WO 03/101514 A1 | 12/2003 |
| EP | | 0 114 617 A2 | 8/1984 | WO | WO 03/103759 A1 | 12/2003 |
| EP | | 0 063 599 | 6/1986 | WO | WO 2004/089451 A1 | 10/2004 |
| EP | | 0 230 323 B1 | 7/1987 | WO | WO 2006/110080 A1 | 10/2006 |
| EP | | 0 236 871 A2 | 9/1987 | | | |
| EP | | 0 269 496 A2 | 6/1988 | | | |
| EP | | 0 280 104 B1 | 8/1988 | | | |
| EP | | 0 488 609 A1 | 6/1992 | | | |
| EP | | 0 559 757 B1 | 9/1993 | | | |
| EP | | 0 949 584 A2 | 10/1999 | | | |

OTHER PUBLICATIONS

International Search Report in International Application No. PCT/IB03/01032, dated Aug. 19, 2003, 10 pages.

\* cited by examiner

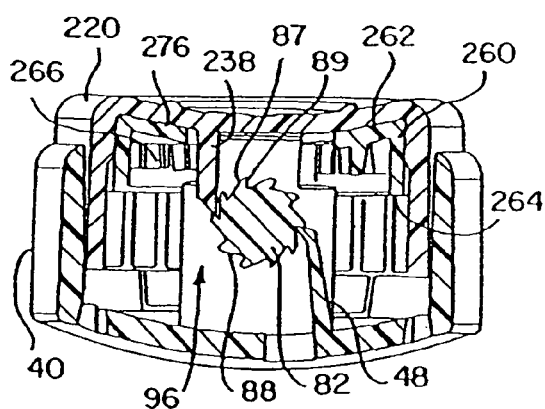
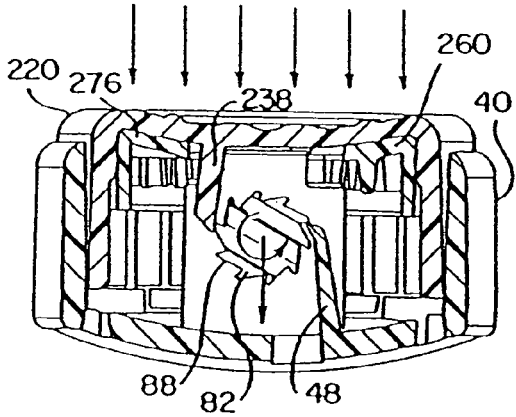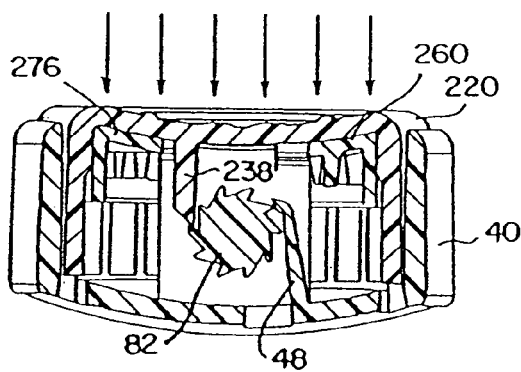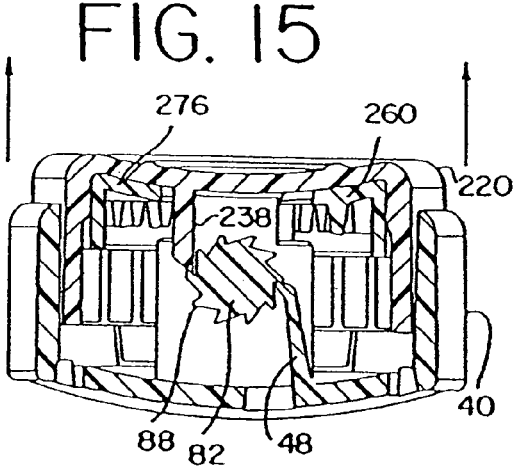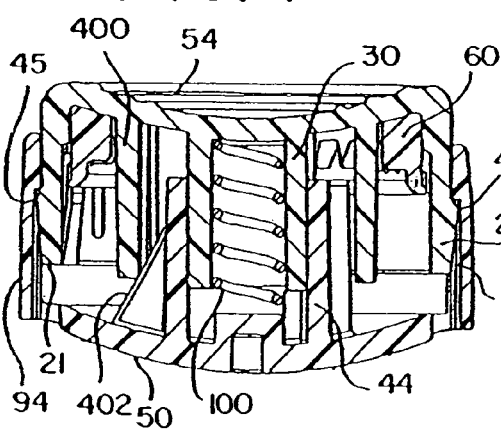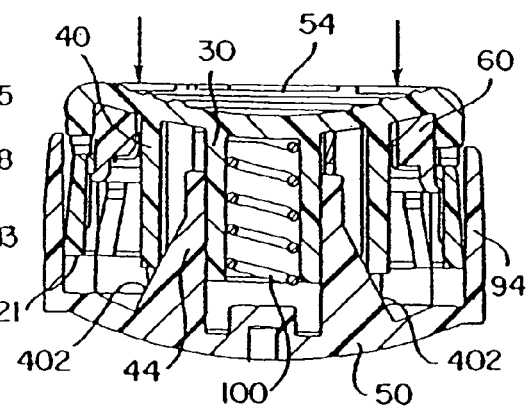

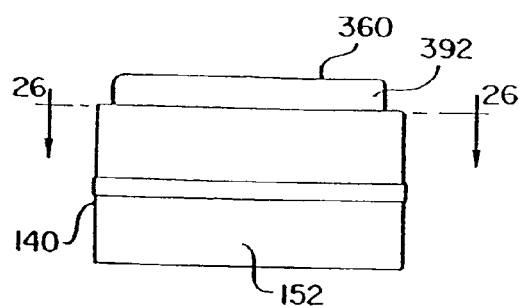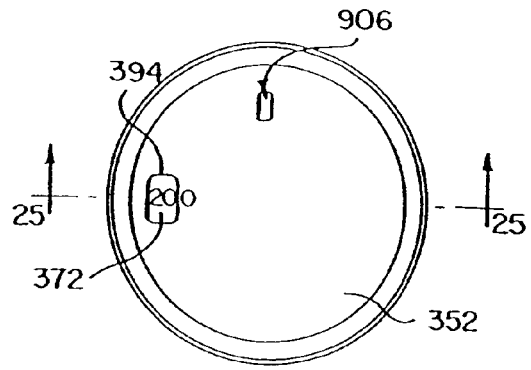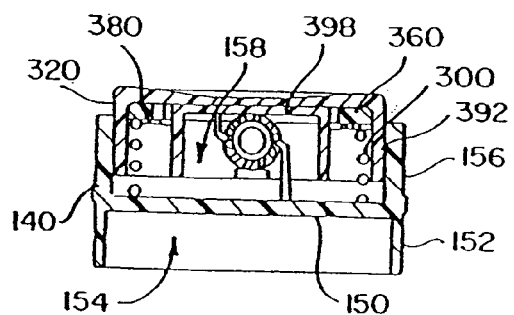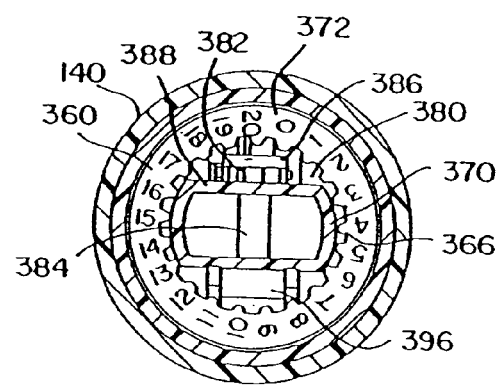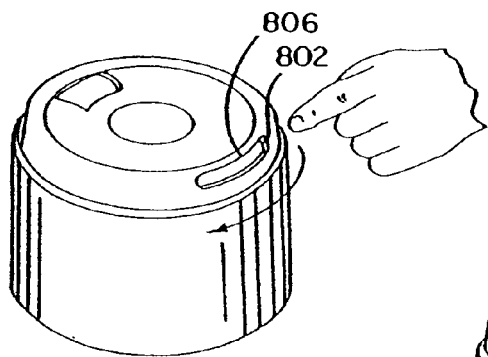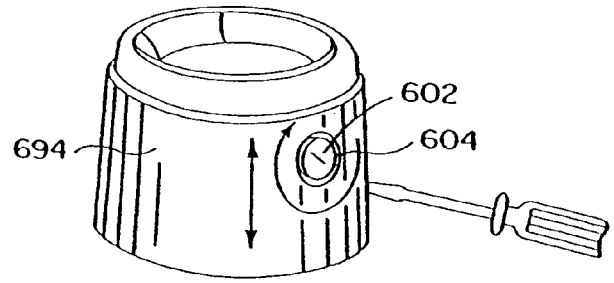

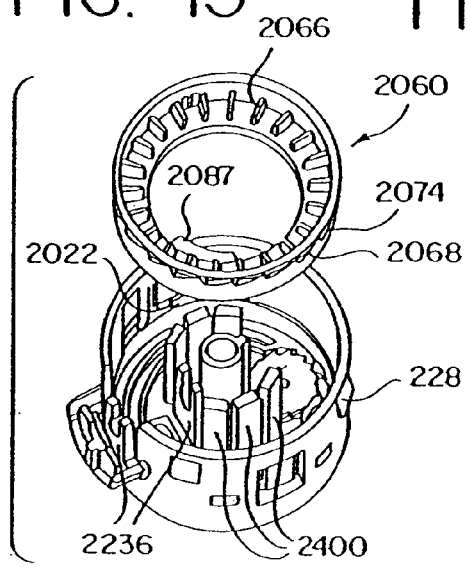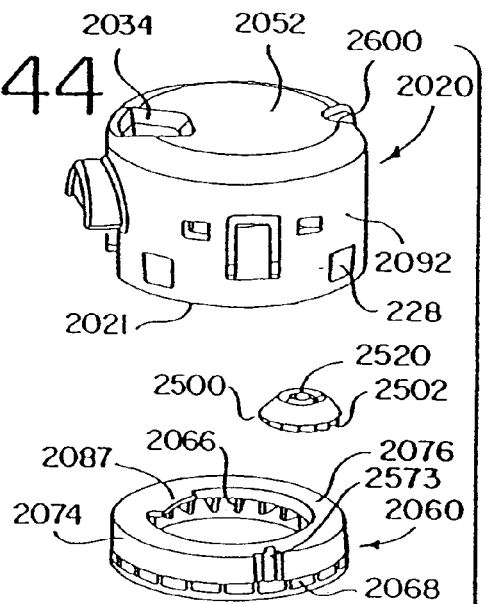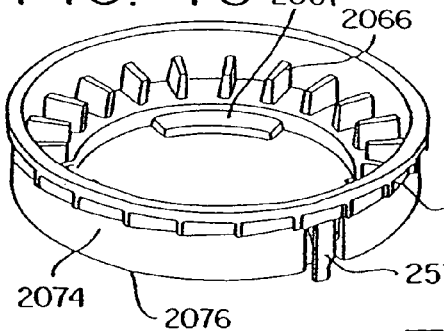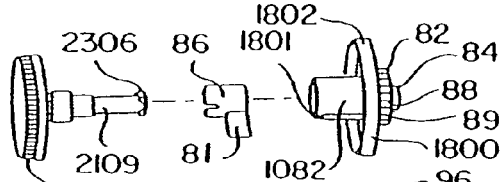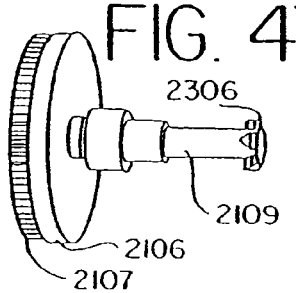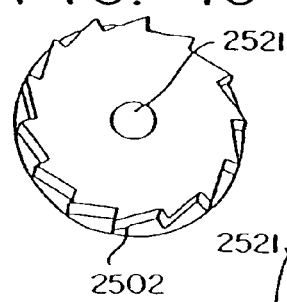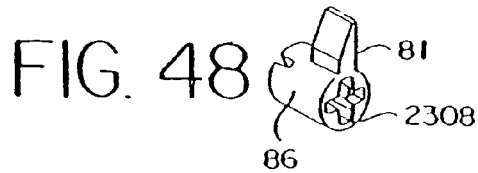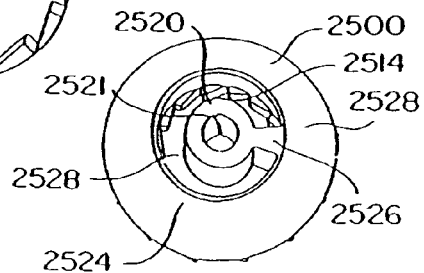

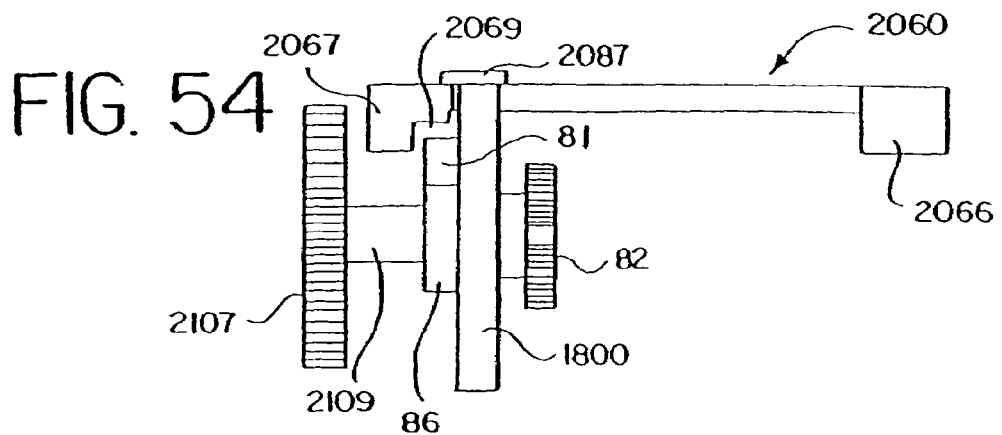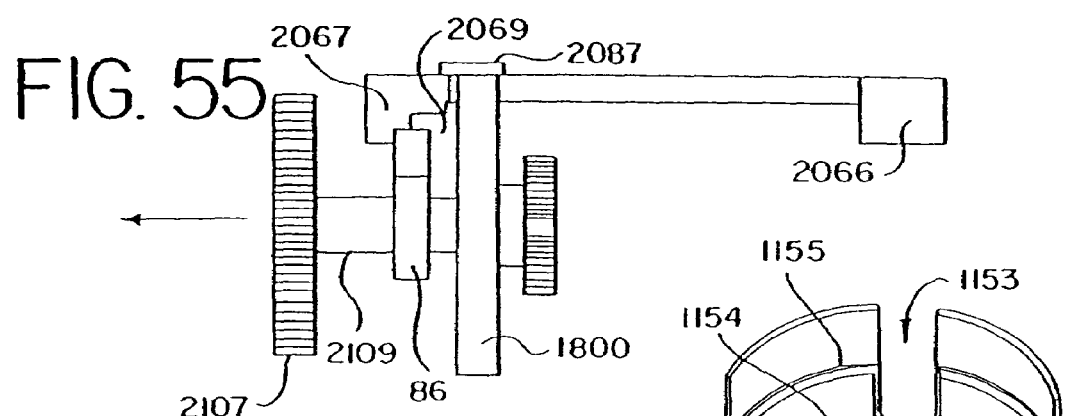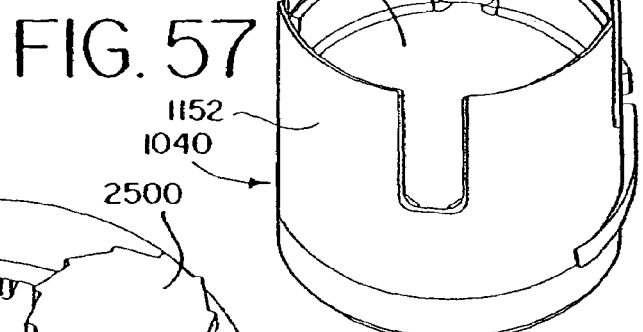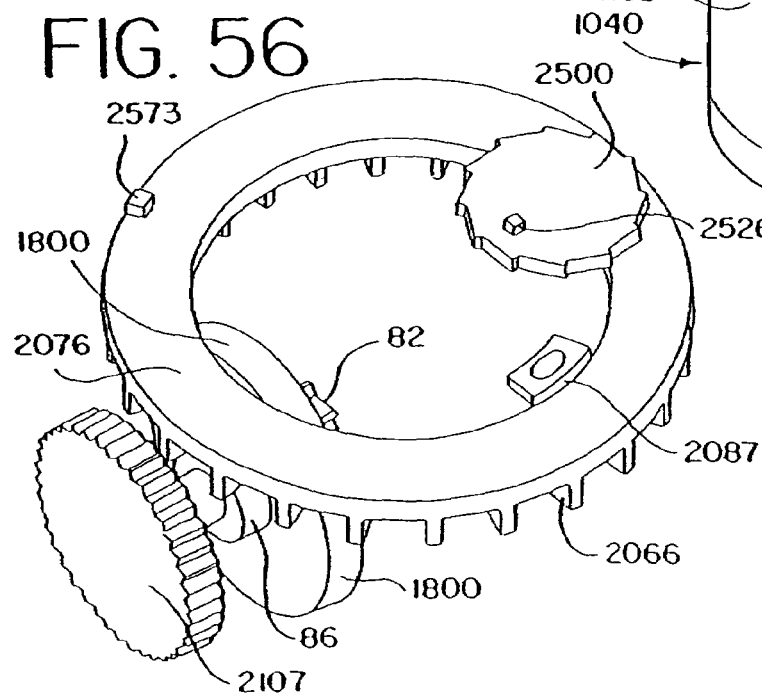

INDICATING DEVICE

This application is a continuation of application Ser. No. 10/876,005, filed Jun. 24, 2004, now U.S. Pat. No. 6,926,002, which is a continuation of application Ser. No. 10/409,247, filed Apr. 8, 2003, now U.S. Pat. No. 6,953,039, which is continuation of application Ser. No. 10/039,744, filed Oct. 26, 2001, now issued as U.S. Pat. No. 6,761,161, which is a continuation of application Ser. No. 09/303,043, filed Apr. 30, 1999, now issued as U.S. Pat. No. 6,336,453, and which also is a continuation-in-part of application Ser. No. 09/603,427, filed Jun. 26, 2000, now issued as U.S. Pat. No. 6,328,037, which is a continuation of application Ser. No. 09/073,275, filed May 5, 1998, now issued as U.S. Pat. No. 6,082,358, the entire disclosures of which are hereby incorporated by reference.

BACKGROUND OF THE INVENTION

The present invention relates generally to an indicating device for indicating the number of metered dosages that have been dispensed from, or remain in, an aerosol container, and in particular, to an indicating device adapted to be mounted to the aerosol container.

Aerosol dispensing devices have been developed that include a dose indicating device to indicate the number of metered doses that have been dispensed from the device, or to indicate the number of doses remaining therein. For example, patients have certain conditions that can be treated with medicaments dispensed in an aerosol and administered to the patient by inhalation. In one format, the aerosol with medicaments are contained in a container, and dispensed in metered, or measured, dosages with an inhalation device, or actuator boot. In such an arrangement, it can be important for the patient to be able to ascertain the number of metered doses remaining in the container, either by an indication of the number remaining therein or by knowledge of the number already dispensed therefrom, such that the patient is not caught unaware with an empty container when in need of the medicament. Thus, it may be important for the inhalation device to provide an accurate indication of either the number of doses remaining in the container, or the number of doses already dispensed therefrom.

Typically, a conventional aerosol container includes a body and a valve stem which can be depressed relative to the body so as to emit the metered dose of aerosol and medicament. The container typically is supplied with a predetermined number of metered doses, generally on the order of about 200, such that the counting of the number of valve stem depressions, and corresponding number of dispensed metered doses, can be directly correlated with the number of doses remaining in the container.

In operation, the container is typically received within a housing of the inhalation device, wherein the valve is brought into engagement with a support block in the housing. The user administers the medicament by moving the container relative to the housing so as to depress the valve stem and internal valve and thereby release a metered dose, which is typically administered to the user through a port or mouthpiece extending from the housing. After the dose is administered, the valve stem, which is typically spring loaded, biases the container away from the support block so as to again move the container relative to the housing. In this way, a metered dose of medicament is administered by each cycle of linear reciprocal movement of the container relative to the housing.

Some actuator boots, or other devices attached to the medicament container, have indicating devices that convert the linear reciprocal movement of the container relative to the housing into a one-way, or single-cycle, movement of an indicator, wherein the indicator identifies the relative fullness of the container, the number of metered doses remaining therein or the number of doses already administered. Although these actuator boots with indicators, or separate indicator devices, have provided the advantage of generally being able to keep track of the number of dosages, there remains room for improvement. For example, indicating devices of this nature may include complex moving parts which can be difficult to assemble and expensive to manufacture. Such devices may also be susceptible to counting inaccuracies due to the configuration of the indexing or mating parts, or require excessive amounts of space within the housing to accommodate the relatively large or numerous moving parts. Others still may impede or interfere with the airflow and medicament being dispensed from the inhalation device. Alternatively, some devices use electrical circuitry to count or record the dispersements. Such devices can be relatively expensive to manufacture, however, and typically require a power source which may be susceptible to damage in various environments, such as moist conditions.

SUMMARY OF THE INVENTION

Briefly stated, the invention is directed to an indicating device for indicating the number of metered doses that have been dispensed from or remain in a container. The container has a valve stem extending longitudinally therefrom; the valve stem being moveable between a closed position and an open position. The container dispenses a metered dosage when the valve stem is moved to the open position. The indicating device includes a base member adapted to be mounted to the container, a cap member moveably connected to the base member, an indicator member rotatably mounted to the cap member and a drive member adapted to rotate the indicator member an incremental amount upon a predetermined number of axial movements of the cap member relative to the base member.

In a preferred embodiment, the cap member is moveable relative to the base member along an axial path. The indicator member has a plurality of teeth and is rotatably mounted to the cap member about an axis substantially parallel to the axial movement of the cap member relative to the base member. A drive mechanism, including the drive member, comprises a ratchet wheel rotatably mounted to one of the base member and cap member about an axis substantially perpendicular to the axis defined by the axial movement of the cap member relative to the base member. The drive member is coaxially mounted with the ratchet wheel and a pawl is mounted to one of the cap member and base member. The pawl is selectively engaged with the ratchet wheel upon each axial movement of the cap member relative to the base member so as to rotate the ratchet wheel and drive member an incremental amount. The drive member is selectively engaged with at least one of the plurality of indicator member teeth upon a predetermined number of axial movements of the cap member relative to the base member such that the indicator member is rotated an incremental amount.

In another aspect, the indicating device comprises a first and second indicator member, with each of the first and second indicator members mounted to the cap member about an axis substantially parallel to the axial movement of the cap member relative to the base member. The first indicator member selectively engages the second indicator member as the first indicator member completes a usage cycle, representing one complete use of the indicating device and attached container, so as to rotate the second indicator member an incremental amount In a preferred embodiment, the first indicator member comprises dosage indicia indicating the number of doses that have been dispensed from or remain in the container, while the second indicator member comprises usage indicia indicating the number of usage cycles that have been completed for the indicating device, or the number of usage cycles remaining therefor.

In yet another aspect, the indicating device comprises a first indicator mounted to the cap member about an axis substantially parallel to the axial movement of the cap member relative to the base member and a second indicator member mounted to one of the cap member and the base member about an axis substantially perpendicular to the axial movement of the cap member relative to the base member. In a preferred embodiment, both the first and second indicator members comprise dosage indicia indicating the number of doses that have been dispensed from or remain in the container, with the second indicator member rotating an incremental amount in response to each axial movement of the cap member relative to the base member and the second indicator member rotating an incremental amount upon a predetermined number of axial movements of the cap member relative to the base member.

In another aspect, the indicating device comprises a first and second indicator member mounted to the cap member about an axis substantially parallel to the axial movement of the cap member relative to the base member and a third indicator member mounted to the cap member about an axis substantially perpendicular to the axial movement of the cap member relative to the base member. In a preferred embodiment, the first and third indicator members comprise dosage indicia, while the second indicator member preferably comprises usage indicia.

In yet another aspect, the indicating device comprises a reset member connected to one of the drive member and indicator member. The reset member can be rotated to move the indicator member relative to the cap member independent of any axial movement of the cap member relative to the base member.

In another aspect of the invention, a method is provided for indicating the number of measured dosages dispensed from or remaining in the container. The method includes the steps of providing a housing for moveably supporting the container and providing an indicating device having a cap member, a base member and an indicator member rotatably mounted to the cap member. The method further comprises the steps of moving the cap member toward the base member so as to move the container along the longitudinal axis and thereby move the valve stem to the open position wherein a metered dosage is discharged, moving the cap member away from the base member, and moving the indicator member in response to the movement of the cap member relative to the base member.

Referring to a preferred embodiment, the method further includes the steps of engaging the ratchet wheel with the pawl upon one of the movements of the cap member toward and away from the base member and engaging the indicator member with the drive member so as to rotate the indicator member.

In yet another aspect, a method is provided for assembling a dispenser for dispensing metered dosages of medicaments from a container. The method includes the steps of providing a housing, disposing a container in the housing and mounting an indicating device to the container.

The present invention provides significant advantages over other aerosol dispensing devices and indicating devices used therewith. In particular, the indicating device can be separately manufactured and installed as needed on any number of conventional types of aerosol containers with little or no required modification to the container or housing Moreover, the indicating device with its indicator member and drive mechanism is comprised of a relatively few, simple mechanical parts that are relatively easy to manufacture and assemble In this way, the indicating device is made more robust and is less susceptible to damage when exposed to various adverse user environments. In addition, the drive mechanism and indicator member provide a reliable indicating device for indicating the number of doses dispensed from or remaining in the container, and the indicating device can be made in a relatively compact configuration that does not interfere with the use of the dispensing device.

The present invention, together with further objects and advantages, will be best understood by reference to the following detailed description taken in conjunction with the accompanying drawings

BRIEF DESCRIPTION OF THE DRAWINGS

FIG. 12 is a cross-sectional view of the indicating device taken along line 12-12 of FIG. 11, wherein the cap member is in a fully extended position relative to the base member prior to the application of an axial force by the user.

FIG. 13 is a cross-sectional view of the indicating device similar to FIG. 12 but with the cap member shown as moving toward the base member at an intermediate position of the stroke as indicated by the directional arrows.

FIG. 14 is a cross-sectional view of the indicating device similar to FIG. 12 but with the cap member reaching the bottom of the stroke as indicated by the directional arrows.

FIG. 15 is a cross-sectional view of the indicating device similar to FIG. 12 showing the cap member as it returns to the fully extended position relative to said base member as indicated by the directional arrows.

FIG. 16 is a cross-sectional view of the indicating device taken through the middle of the indicating device and showing engagement members disposed in pockets formed in the base member.

FIG. 17 is a cross-sectional view of the indicating device taken through the middle of the indicating device and showing an alternative return mechanism for the cap member.

FIG. 23 is a side view of an alternative embodiment of the indicating device.

FIG. 24 is a top view of the indicating device shown in FIG. 23.

FIG. 25 is a cross-section view of the indicating device taken along line 25-25 of FIG. 24.

FIG. 26 is a cross-section view of the indicating device taken along line 26-26 of FIG. 23.

FIG. 27 is a perspective view of an indicating device with a reset device.

FIG. 28 is a perspective view of an indicating device with an alternative embodiment of the reset device.

FIG. 44 is an exploded perspective view of an alternative embodiment of an indicating device having indicator members with dosage indicia and an indicator member with usage indicia.

FIG. 45 is a bottom perspective view of the cap member shown in FIG. 44 with a usage indicator member installed therein and a dosage indicator member exploded out therefrom.

FIG. 46 is a bottom perspective view of a dosage indicator member shown in FIG. 44.

FIG. 47 is a perspective view of a reset assembly shown in FIG. 44.

FIG. 48 is a perspective view of the drive member shown in FIG. 44.

FIG. 49 is a bottom perspective view of the usage indicator member shown in FIG. 44.

FIG. 50 is a top perspective view of the usage indicator member shown in FIG. 44.

FIG. 54 is a side view of a first and second dosage indicator member with the reset member and drive member in a disengaged position.

FIG. 55 is a side view of a first and second dosage indicator member with the reset member and drive member in an engaged reset position.

FIG. 56 is a top perspective view of a first and second dosage indicator member, a usage indicator member and a drive assembly.

FIG. 57 is a bottom perspective view of the base member shown in FIG. 38.

DETAILED DESCRIPTION OF THE PRESENTLY PREFERRED EMBODIMENTS

Figure 31:
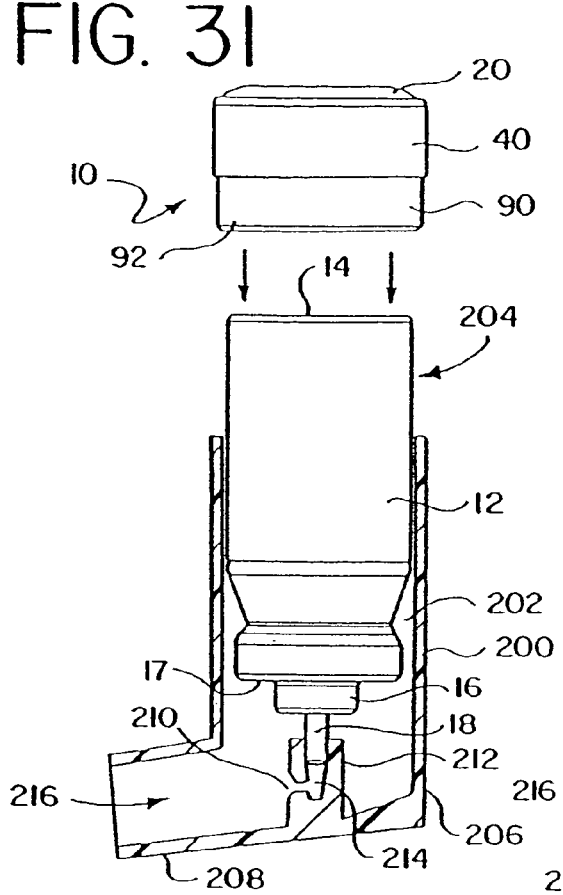
FIG. 31 is an exploded side view of an indicating device and adapter being applied to the bottom of a container supported in a dispenser housing shown in cross-section.
Figure 32:
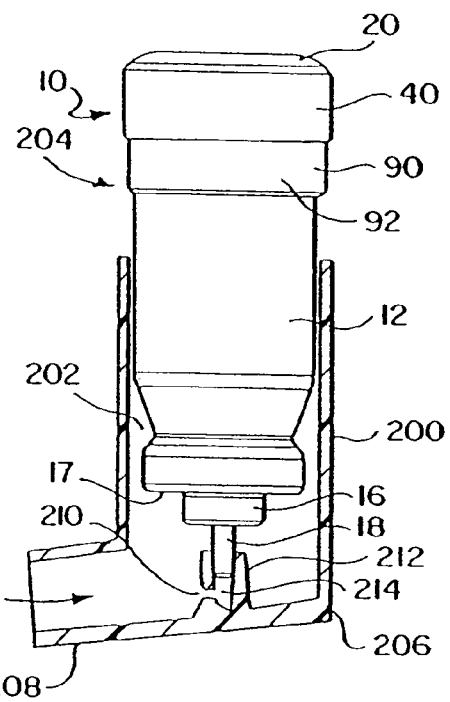
FIG. 32 is a side view of an indicating device having an adapter applied to the bottom of a container supported in a dispenser housing shown in cross-section.

Referring to the drawings, and in particular FIGS. 31 and 32, an aerosol dispenser is shown as including a housing 200, or actuator boot, and a container 12 disposed therein. The housing has a longitudinally extending cavity 202 shaped to receive the container. A top portion of the housing is generally open such that the container can be inserted in the housing through opening 204 and be installed therein with a bottom end 14 of the container protruding from the housing so as to be exposed to the user for actuation.

The terms "longitudinal" and "axial" as used herein are intended to indicate the direction of the reciprocal movement of the container relative to the housing, and of an indicating device cap member relative to a base member. The terms "top," "bottom," "upwardly" and "downwardly" are intended to indicate directions when viewing the inhalation devices as shown in the Figures, but with the understanding that the container is inverted such that the top surface thereof is located adjacent the bottom of the housing and vice versa Moreover, it should be understood that a user can use the container and dispenser in any number of positions, including but not limited to the preferred upright position shown in FIGS. 31 and 32.

As shown in FIGS. 31 and 32, a cylindrical support block 212 having a well 214 is formed in a bottom portion 206 of the housing. An orifice 210 penetrates the support block to communicate with a bottom portion of the well. In one embodiment, a mouthpiece 208, intended for insertion into the mouth of a patient, forms an exhaust port 216 that communicates with the orifice and well. The mouthpiece 208 extends laterally from the housing so as to facilitate insertion of the mouthpiece into the mouth of the patient.

The container 12 is cylindrical and has a hub 16 disposed on a top surface 17 thereof. A valve stem 18 extends longitudinally from the hub. The valve stem extends coaxially from the container and is biased outwardly therefrom by a spring (not shown) mounted within the valve stem of the container. The container 12 is mounted in the housing by press fitting the valve stem 18 in the well 214 of the support block In a preferred embodiment, the container 12 is filled with a pressurized aerosol and medicament which is dispensed therefrom in specific metered doses by depressing or moving the valve stem 18 from an extended closed position to a depressed open position. A single metered dose is dispensed from the container by each reciprocal, longitudinal movement of the valve stem.

In operation, the opening of the valve stem is effected by moving the container 12 reciprocally within the housing 200 along a longitudinal axis, defined by the valve stem and the reciprocal movement of the container, by depressing the bottom end 14 of the container relative to the housing so as to move the valve stem 18 to the open position as it is supported within the well by the support block. As the valve stem is moved to the open position, the container dispenses a metered dose of aerosol and medicament through the well 214 and orifice 210. The aerosol and medicament are then transmitted to the patient through the exhaust port 216 of the mouthpiece by way of either a self-generated or assisted airflow.

In other delivery systems, the housing and holder for the container are attached to a component having a chamber with an output end. Examples of these kinds of delivery systems are shown for example in U.S. Pat. No. 5,012,803, issued May 7, 1991, and U.S. Pat. No. 4,460,412, issued Sep. 11, 1984, both of which are hereby incorporated herein by reference. (No license, expressed or implied, is intended to be granted to either of these patents by reason of the incorporation by reference herein). In these kinds of delivery systems, the component having the chamber can be adapted to receive the mouthpiece of the housing, or it can be integrally connected with a holder supporting the container. In either embodiment, the metered dose of medicament in aerosol is first dispensed from the container into the chamber, and thereafter inhaled by the patient.

In a preferred embodiment, the container 12 is intended to dispense a predetermined number of metered doses of medicament. For example, conventional inhaler containers typically hold on the order of 100 to 200 metered doses. It should be understood, however, that the range of available doses could potentially vary from as few as one dose to as many as 500, or even more, depending, for example, on the capacity of the container, and/or the size of the metering dose valve. In operation, it can be important for the patient to be aware of the number of metered doses remaining in the container such that the patient is not caught unaware with an empty container when in need of the medicament.

Now generally referring to the Figures, a dose indicating device is shown. The indicating device 10 indicates the number of metered doses that have been dispensed from or remain in the container. As shown in the embodiments of FIGS. 1-3A and 10-11, respectively, the indicating device 10, 200, 500 includes an indicating device housing comprised of a cap member 20, 220, 520 disposed in a base member 40, 540. The base member 40 is configured such that it can be mounted to the bottom of the container 12. In a first embodiment, shown in FIGS. 2, 6 and 12-17, the base member includes a convex, or curved bottom portion 50, or floor, which is shaped to be received in and to mate with the bottom end 14 of the container, which has a concave or inwardly curved contour (see FIG. 2). The base member 40 is preferably bonded to the bottom of the container with adhesive, double sided tape, or similar bonding agent. As shown in FIGS. 6 and 10-15, a circumferential skirt member 94 extends upwardly from the base portion to form a cavity 96.

Alternatively, as shown in FIG. 25, the base member 140 includes a bottom portion 150, a downwardly depending circumferential skirt 152 and an upwardly depending circumferential skirt 156. Depending skirt 152 forms a recess or cavity 154 which is shaped to receive the bottom end of the container. The base member is mounted on the container either by bonding one or more of the bottom portion or skirt to the container, or by press fitting the container in the cavity 154 so as to provide an interference fit between the container and the depending skirt. The upwardly depending skirt 156 and bottom portion form an upper cavity 158 overlying the lower cavity 154.

In yet another embodiment, shown in FIGS. 29-32, an adapter member 90 is attached to one of the above-mentioned base members by way of bonding, an interference fit, a snap fit, or a threadable engagement. The adapter member 90 preferably has a cylindrical configuration and comprises a circumferential skirt 92 that is shaped to receive the bottom end of the container. Again, the adapter can be mounted to the container by way of bonding, an interference fit, or both. Adapters having different internal diameters can be provided such that a single indicating device having a modular base member can be mounted on various aerosol containers having a variety of outer diameters.

Alternatively, as shown in FIG. 57, the base member 1040 includes a downwardly depending circumferential skirt 1152 forming a recess 1154. The skirt 1152 includes one or more steps 1155 or shoulders, which form various inner diameters in the base member 1040 In this way, a single base member 1040 can be used with containers having different diameters. It should be understood that although only one step is shown, so as to thereby form two inner diameters on the skirt 1152, the base member could be configured with additional steps so as to provide a plurality of various inner diameters dimensioned to receive various containers by way of a friction fit. The skirt 1152 is also configured with a plurality of cut-outs, or slits 1153, which permit enhanced air flow around the base member in embodiments where the base member may be in close proximity to the area where the medicament or aerosol is being dispensed Although the disclosed container and indicating device, and in particular, the cap member and base member, are shown as preferably having a circular cross section, those skilled in the art should understand that the container and indicating device, including any adapter, can be configured in other shapes, including for example, but not limited to, a rectangular or triangular cross-section.

Figure 1:
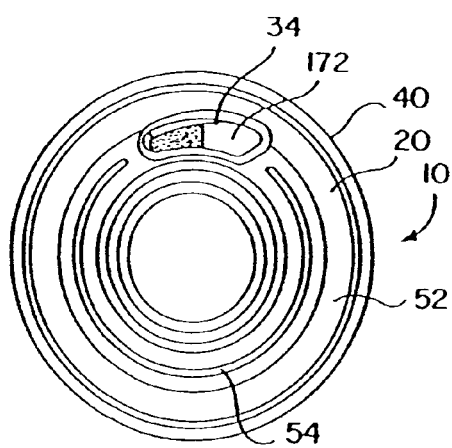
FIG. 1 is a top view of an indicating device having a viewing window.
Figure 1A:
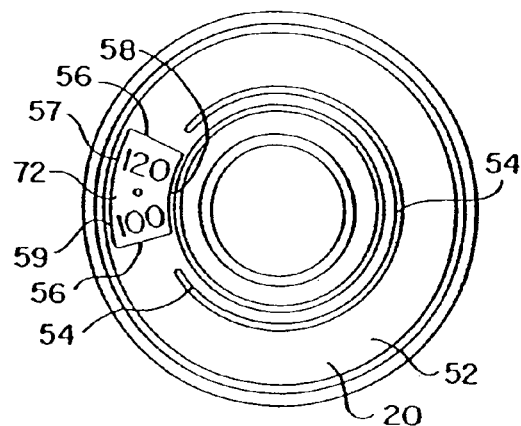
FIG. 1A is a top view of the indicating device showing an alternative embodiment of the viewing window with indicia visible therethrough.
Figure 1B:
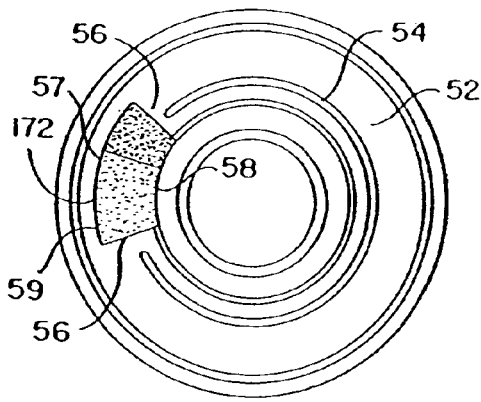
FIG. 1B is a top view of the indicating device showing an alternative embodiment of the indicia.
Figure 2:
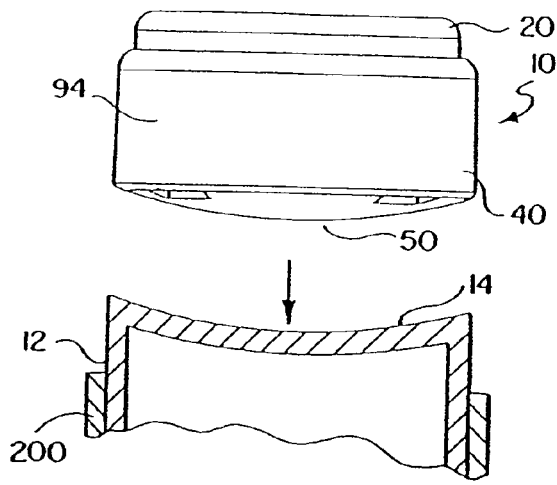
FIG. 2 is a side view of the indicating device being mounted to the top of a container shown in cross-section.

As best shown in FIGS. 1, 1A and 1B, the cap member 20 has a top portion 52 with a viewing window 34, 59 formed therein. Preferably, the cap member 20 is circular and the viewing window is formed in the top portion adjacent the outer periphery of the cap member so as to overlie indicia applied to the top of an indicator member supported beneath the cap member. The viewing window can be configured in a number of various shapes. For example, the viewing window 34 can be tapered as shown in FIG. 1, or it can be an arcuate shaped window 59 bounded by coaxial inner and outer curved borders 57, 58 and radial side borders 56 as shown in FIGS. 1A and 1B. The top of the cap member preferably has a plurality of raised portions 54 forming a grippable pattern for the user's thumb, or finger. In this way, the user can firmly press down on the cap member without slippage. One of skill in the art should recognize that other patterns or grippable surfaces, such as a knurled pattern, can be applied to the cap member to facilitate the use of the indicating device.

Referring to FIGS. 4, 6, 38 and 44 the cap member 20, 220, 1020, 2020 comprises a circumferential skirt 92, 292, 1092, 2092 depending downwardly from the top portion 52, 252, 1052, 2052. The skirt preferably has a smaller diameter than the upwardly depending skirt of the base member, such that the cap member skirt nests within the upwardly extending skirt of the base member. Alternatively, the cap member can be configured with a skirt having a larger diameter than the skirt of the base member such that the base member skirt nests in the cap member skirt. The cap member 20, 220, 1052, 2052 is moveably mounted to the base member 40, 1040, 2040 by way of a snap fit.

In particular, as shown in FIGS. 5, 6, 7, 9, 10, 16, 29 and 44 the cap member includes a plurality of engagement members 28, 228, 428 extending from an outer circumferential surface of the skirt. The cap member 20, 220, 420 is inserted axially within the recess or cavity 96 of the base member such that the engagement members 28, 228, 428, which have a tapered surface, slide past the rim 42 of the base member skirt until the engagement members are disposed in a plurality of pockets 43 formed along the inner circumferential surface of the base member skirt to form a snap-lock fit. In particular, the upper surface of the engagement member engages an engagement surface 45 defining the top of the pocket. In this way, the cap member is moveable with respect to the base member along an axial, or longitudinal, path. Alternatively, the rim of the base member can be curved slightly inward such that the engagement members engage the inwardly curved rim portion so as to prevent the cap member from being separated from the base member.

The axial movement of the cap member 20, 220, 1020, 2020 relative to the base member 40 is bounded or constrained by the engagement of the engagement members with the top of the base member pockets (or the base member rim) at a fully extended position and by engagement of a bottom rim 21, 221, 1021, 2021 of the cap member skirt with the upper surface of the bottom portion at the bottom of the stroke as shown for example in FIGS. 12-15. One of skill in the art should understand that the engagement members can alternatively be formed on the base member skirt so as to engage pockets or openings, or a rim (or like protrusion), formed on the cap member skirt.

As shown in FIGS. 6, 9, 16 and 17, a spring 100 is disposed between the cap member and the base member. The spring is preferably disposed in a downwardly extending hub portion 30, 230 of the cap member (shown in FIGS. 4 and 6) and an upwardly extending hub portion 44 (shown in FIGS. 10, 16 and 17) of the base member, which are received one in the other. Alternatively, as shown in FIG. 25, a spring 300 is disposed between the cap member and base member and is of such a size that the coils are positioned adjacent the inner circumferential surface of the cap member skirt 392. The spring 100, 300 functions as a return mechanism and biases the cap member 60, 260, 360 upwardly in the base member such that the engagement members 28, 228 of the cap member engage the upper portion of the pockets of the base member. Although a compression spring is shown in the Figures, it should be understood that a belleville washer, cantilever, torsion, leaf and/or tension springs would also work to bias the cap member upwardly into engagement with the base member. The springs can be made of metal or plastic.

Figure 4:
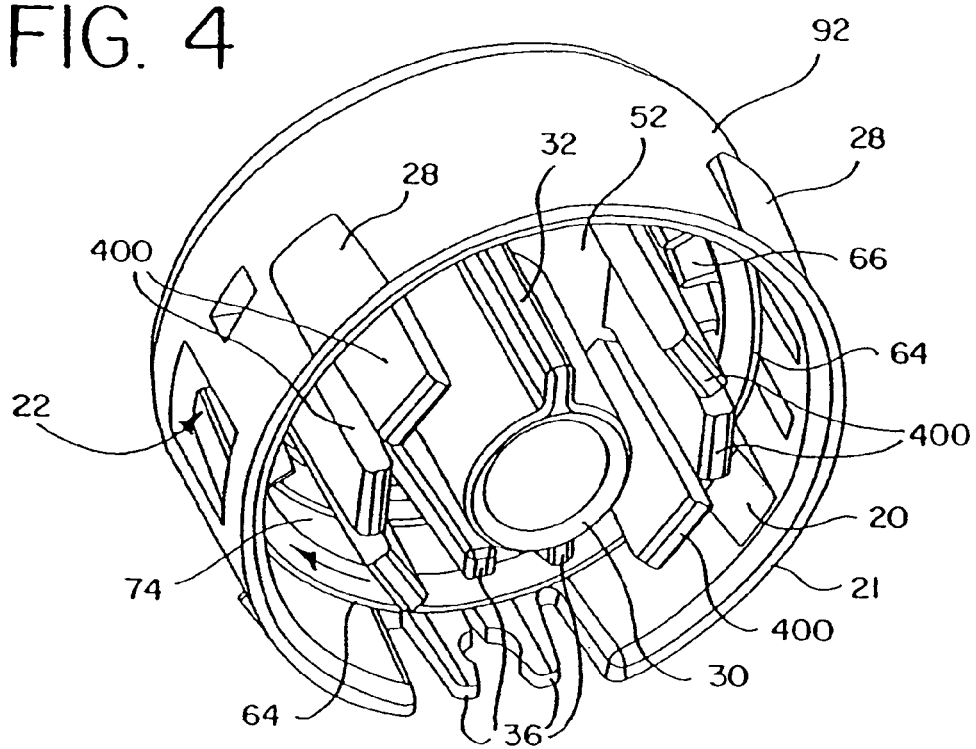
FIG. 4 is a bottom perspective view of the cap member with the indicator member mounted therein.
Figure 5:
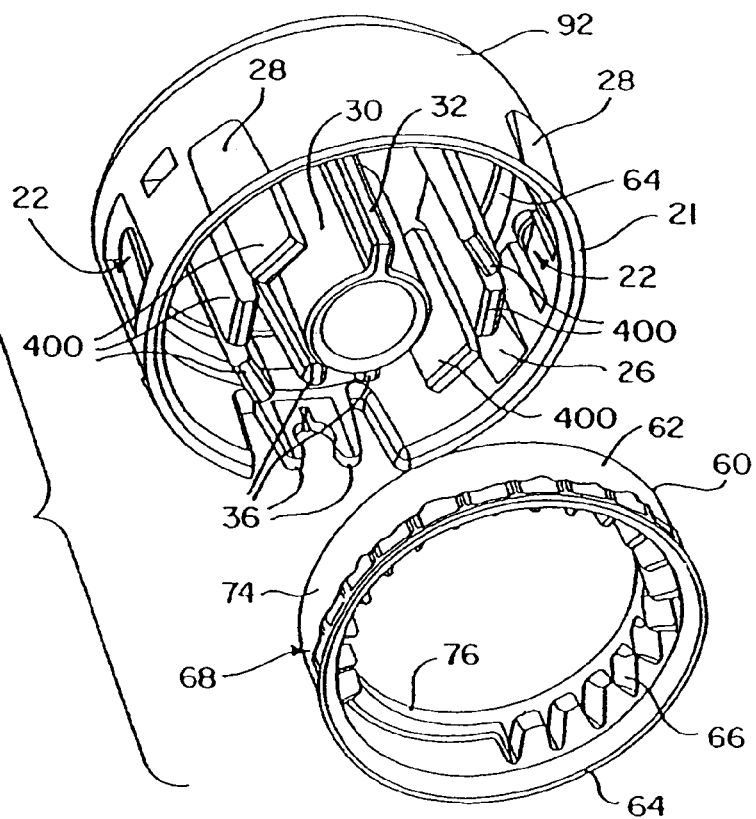
FIG. 5 is an exploded perspective view of the cap member and indicator member shown in FIG. 4.
Figure 39:
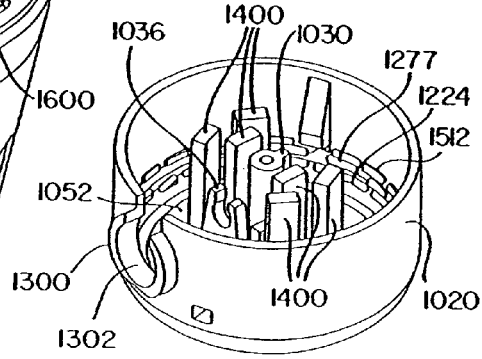
FIG. 39 is a bottom perspective view of the cap member shown in FIG. 38.

As shown in FIGS. 4, 5, 16, 17 and 45, the return mechanism acting between the cap member and base member includes a plurality of resilient arm members 400, 2400 extending downwardly from the cap member. As the cap member is moved toward the base member, one or more of the arm members engages a ramped biasing surface 402 formed along an outer portion of the hub portion 44. The ramped biasing surface biases one or more of the resilient arm members outwardly as the cap member moves toward the base member. As shown in the embodiment of FIGS. 4 and 5, six arm members 400 are arranged circumferentially around the hub portion 30. Alternatively, as shown in the embodiment of FIG. 39, six arm members 1400 are arranged in an "X" pattern around the hub 1030 so as to conserve space and provide additional room under the cap member 1020. Corresponding ramps, or ramped biasing surfaces are similarly arranged in the base member 1140.

The resilient arm member(s) act as cantilever springs to bias the cap member away from the base member when the cap member is released by the user. One of skill in the art should understand that the resilient arm members can also be formed on the base member so as to engage a ramped surface formed on the cap member. One of skill in the art should also understand that the spring and resilient arm members can be used together, as shown in FIGS. 16 and 17, or separately. In addition, it should be understood that one or more arm members and/or ramps may be used, with the size and shape of the arm member and/or ramp members being modified to provide more space between the cap member and base member.

Figure 6:
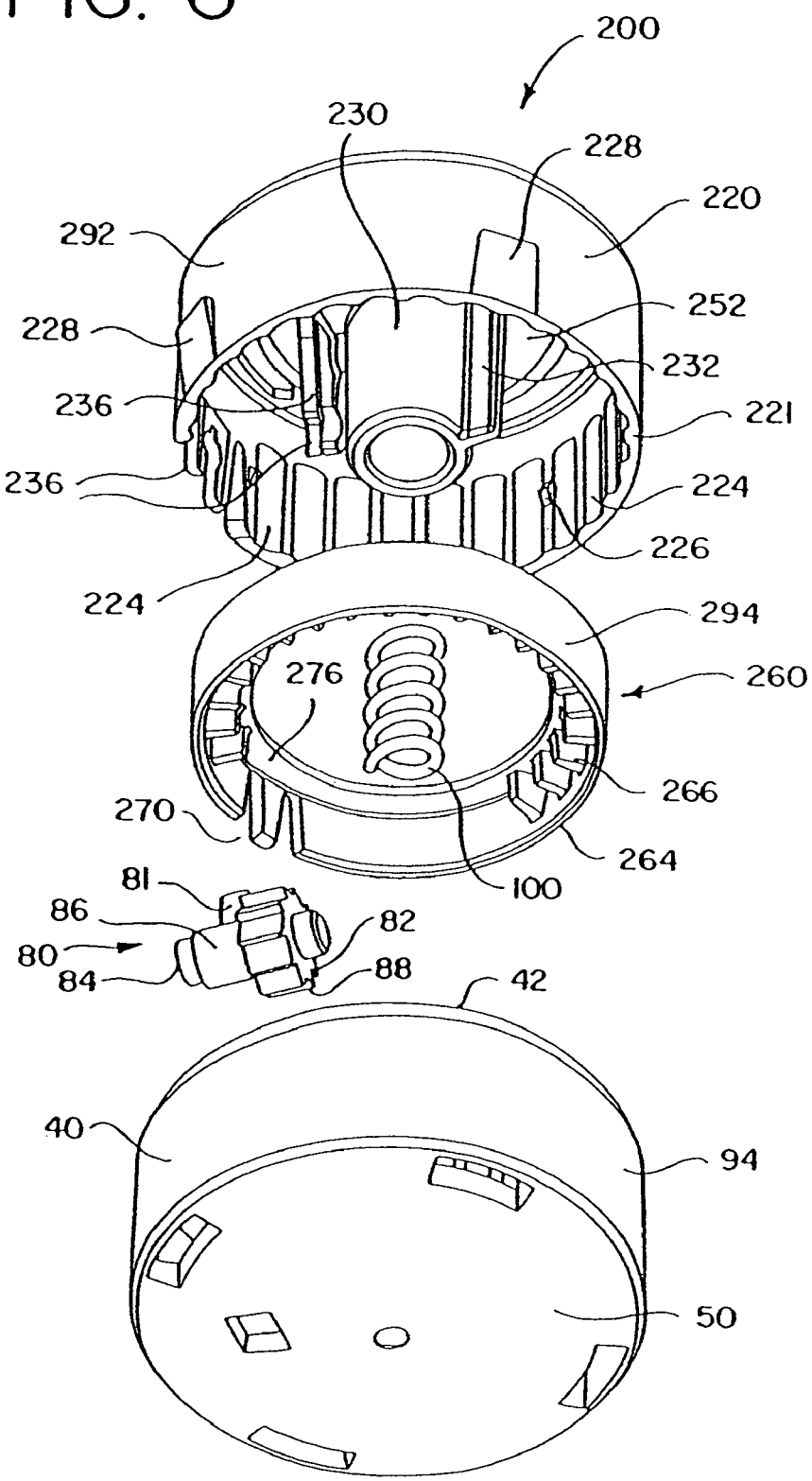
FIG. 6 is an exploded perspective view of an alternative embodiment of the indicating device, including a base member, a cap member, an indicator member, a ratchet wheel and drive member and a spring.
Figure 7:
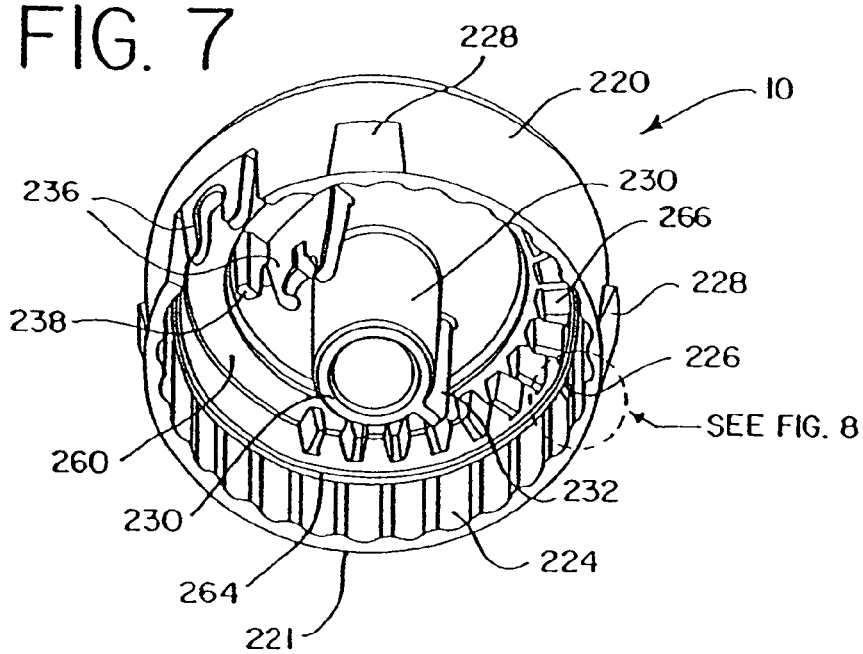
FIG. 7 is a bottom perspective view of the cap member and indicator member of FIG. 6, with the indicator member mounted in the cap member.
Figure 10:
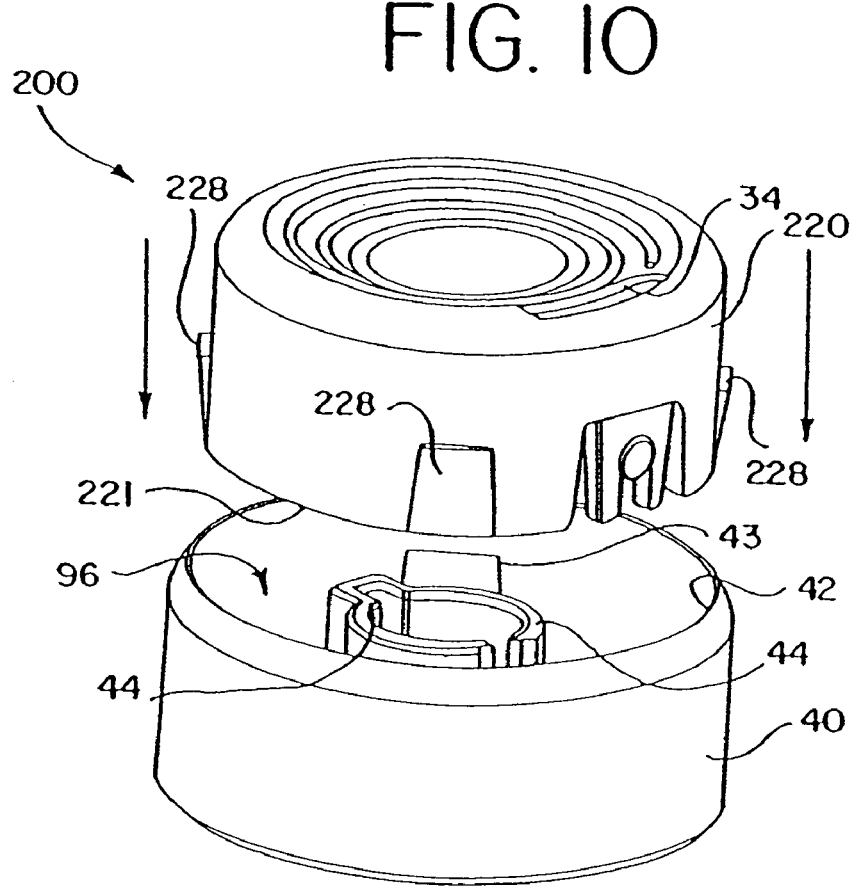
FIG. 10 is an exploded perspective view of the base member and the cap member with the drive mechanism and indicator member mounted therein.
Figure 11:
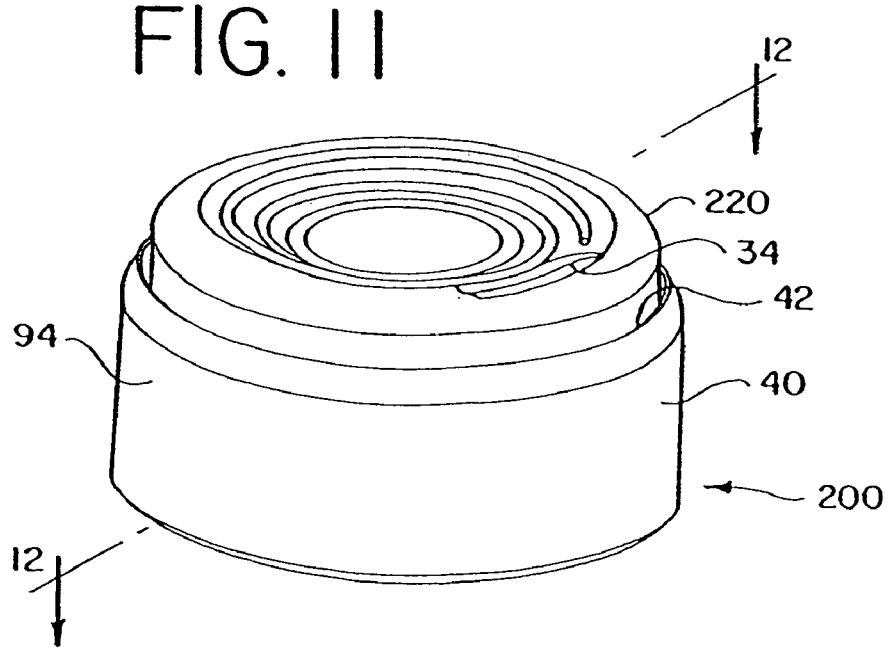
FIG. 11 is a perspective assembly view of the indicating device shown in FIG. 10.
Figure 18:
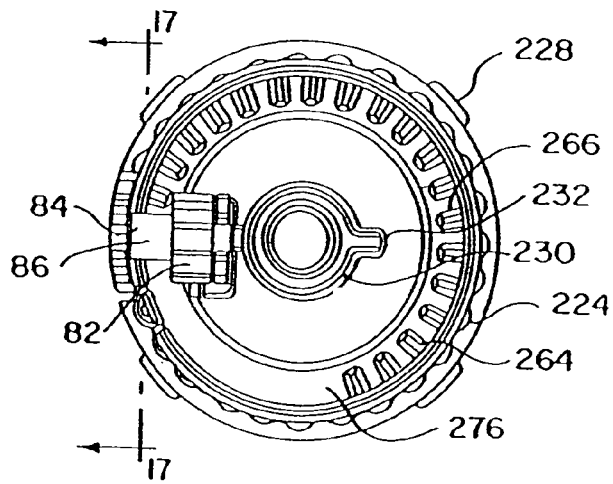
FIG. 18 is a bottom view of the assembly of FIG. 9 (without the spring) at initial setting before a first actuation of the indicator device and container.

As shown in FIGS. 4, 6, and 44 a key member 32, 232, or alignment rib, extends radially from the cap member hub portion 30, 230. As shown in FIG. 10, a key hole 47, or slot, is formed in a radially extending portion of the hub portion 44 of the base member. The slot extends radially from the opening in the hub portion During assembly, the key member of the cap member is received in the key hole of the base member so as to prevent rotation therebetween.

Referring to the various embodiments of FIGS. 4-9, 12-15, 38, 40, and 44-46, a dosage indicator member 60, 260, 1060, 2060 is rotatably mounted in the cap member 20, 220, 1020, 2020 about an axis substantially parallel to the axial movement of the cap member relative to the base member. The indicator member is generally open in the middle and includes a top portion 76, 276, 1076, 2076 having an upper surface 62, 262 that rotatably slides along a bottom surface of the top portion of the cap member. Alternatively, the indicator member can be mounted on the outside of the cap member with a viewing window formed in the indicator member for viewing indicia applied to the top of the cap member.

Figure 8:
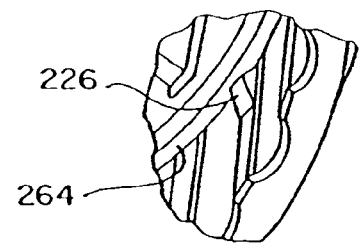
FIG. 8 is an enlarged partial view of the indicator member and cap member of FIG. 7 showing an engagement of the indicator member by the cap member.
Figure 9:
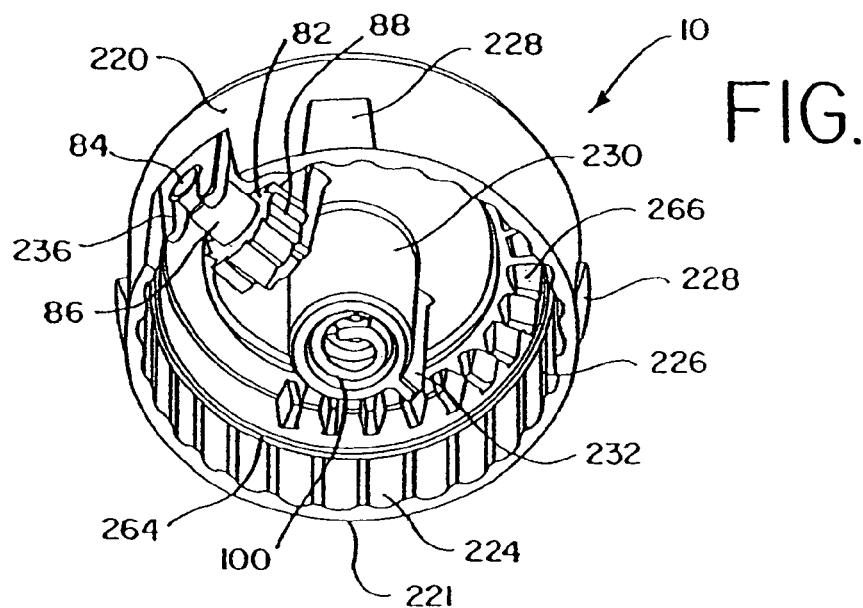
FIG. 9 is a bottom perspective assembly view of the cap member, indicator member, ratchet wheel, drive member and spring shown in FIG. 6.

As shown in the embodiments of FIGS. 5, 6, 38 and 44, the indicator member 60, 260, 1060, 2060 includes a circumferential skirt 74, 274, 1074, 2074 depending downwardly from the top portion. Referring to FIGS. 5 and 8, a plurality of protrusions 26, 226, or engagement tab members, extend from an inner circumferential surface of the cap member skirt and engage a rim 64, 264 formed on the bottom of the indicator member skirt. Alternatively, the indicator member can include an engagement member, or rim, that engages a groove or similar opening in the cap member. In this way, the indicator member is secured to the cap member so as to prevent axial movement therebetween but where the indicator member is permitted to rotate relative to the cap member The indicator member is installed by snap-fitting the indicator member within the cap member One of skill in the art should understand that the indicator member could alternatively be rotatably mounted on the cap member hub portion (having a portion of the key member cut away), or on a similar axle secured to the cap member.

In yet another alternative embodiment, shown in FIGS. 25 and 26, a plate member 380 holds the indicator member 360 against the inner surface of the top portion of the cap member 320 wherein the spring 300 engages a bottom surface of the plate member 380 to bias a top portion 398 of the plate member against the cap member 320 and the cap member away from the base member. The indicator member 360 is nested in the recess formed between an outer flat portion of the plate member and the bottom surface of the cap member. Referring to FIG. 26, the drive assembly is mounted to the plate member 380 by inserting axle 384 through openings in downwardly extending walls 388 of the plate member. An enlarged portion 396 on the end of the axle engages one of the walls, while the ratchet wheel 382 and drive member 386 are mounted to the other end of the axle to complete the assembly. A top portion of the plate member abuts the cap member.

Figure 40:
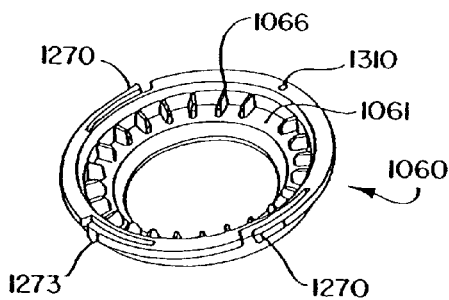
FIG. 40 is a bottom perspective view of a dosage indicator member shown in FIG. 38.

As shown in the embodiments of FIGS. 4-9, 40 and 46 the indicator member 60, 260, 1060, 2060 has a plurality of inwardly facing teeth 66, 266, 1066, 2066 formed around the inner circumference of the skirt As shown in FIGS. 5, 6, and 40, the teeth are preferably formed about only a portion of the circumference, such that a gap 1061 is formed therebetween.

Alternatively, as shown in the embodiment of FIGS. 25 and 26, the indicator member 360 has a plurality of teeth 366 formed radially inwardly about an inner rim of an opening formed in the indicator member, which is configured as a relatively flat ring that does not include a skirt. In yet another embodiment, shown in FIG. 29. the plurality of teeth 466 extend axially downwardly from a ring-like indicator member 460.

As shown in the embodiments of FIGS. 5 and 44-46, the indicator member 60, 2060 includes a plurality of indentations 68, 2068 formed about the outer circumferential surface of the skirt 74, 2074 The cap member includes a pair of upwardly extending resilient indexing members 22, 2022 each having an end portion that engages one of the indentations so as to releasably engage the indicator member and prevent rotation therebetween. The angular distance between the indentations 68, 2068 is substantially the same as the angular distance between the plurality of indicator member teeth 66, 2066. In this way, the indexing member selectively engages the next indentation upon each incremental advancement of the indicator member defined by the distance between adjacent teeth. In the embodiment shown in FIG. 46, the indentations are preferably formed as ratchet teeth which only permit one-way rotation of the indicator member 2060 relative to the cap member.

Figure 38:
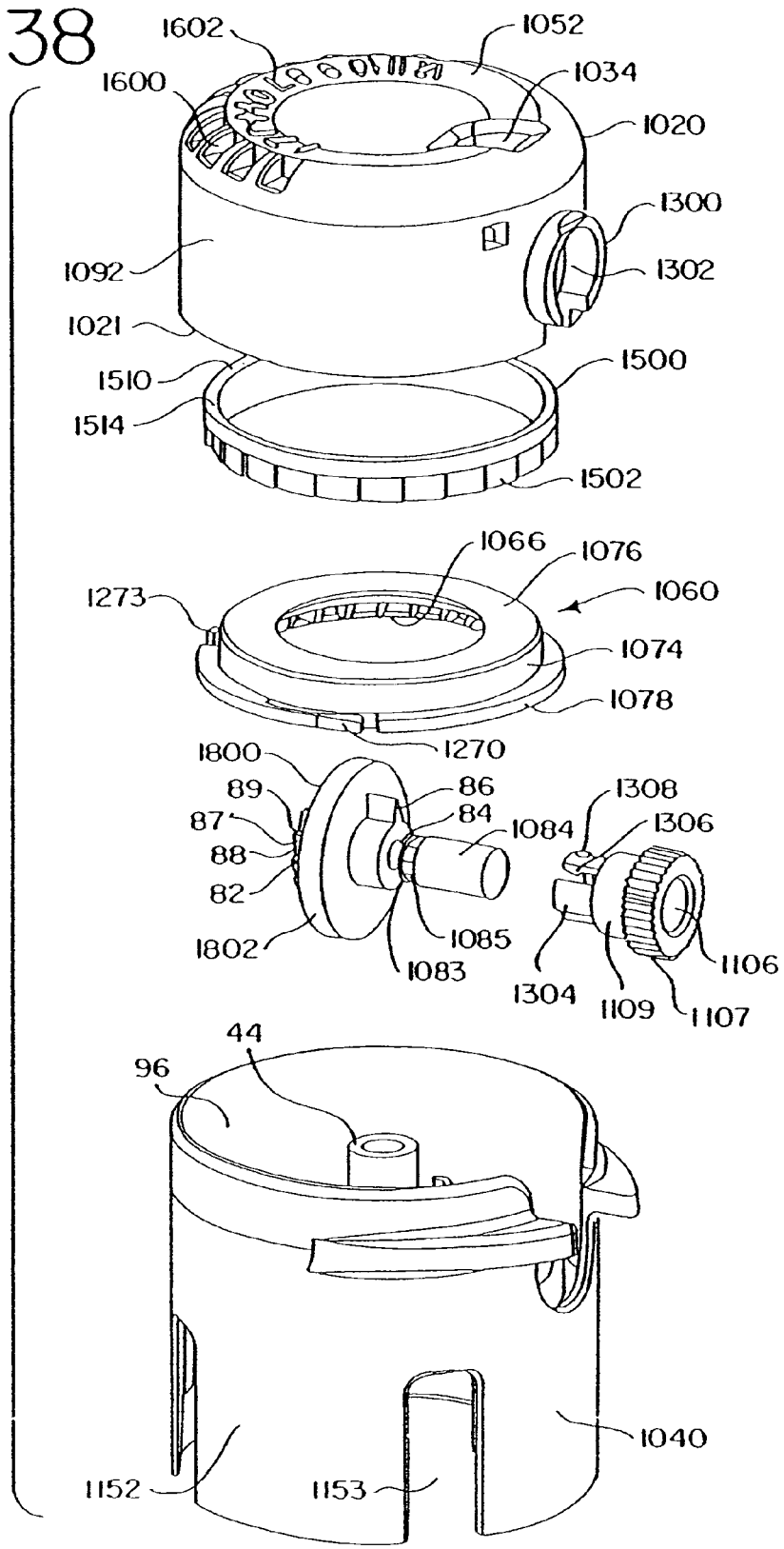
FIG. 38 is an exploded perspective view of the indicating device shown in FIG. 37.

Alternatively, as shown in the embodiments of FIGS. 6 and 38-39, the indentations and indexing member are reversed, i.e., the indentations 224, 1224 are formed about an inner circumferential surface of the cap member skirt and, and shown in FIG. 6, an indexing member 270 depends downwardly from the indicator member in a void formed in the skirt of the indicator member, or, as shown in FIG. 38, a pair of index members 1270 are configured as flexible arms formed along a rim portion 1078 along the bottom edge of the skirt 1074. In the embodiment shown in FIGS. 38, 39 and 40, the interaction between the index members 1270 and the indentations 1224, which are preferably shaped as ratchet teeth, function to index the indicator member by holding it in place between actuations of the cap member and also to prevent the backward rotation of the indicator member 1060. It should be understood that one or more index members can be engaged with a plurality of indentations, preferably formed as ratchet teeth, to control the rotational movement of the indicator member, regardless of whether the index members or indentations are formed on the cap member or the indicator member.

In yet another alternative, shown in FIG. 26, the plate member 380 includes a resilient indexing member 370 that engages one of the plurality of teeth 366 to selectively engage the indicator member so as to prevent the inadvertent rotation thereof. Alternatively, the indexing member can extend from the cap member.

As shown in FIGS. 1A and 1B, dosage indicia 72, 172 in the form of numbers or color codings are provided on the top surface of the indicator member and are visible to the user through the viewing window 34, 59 provided in the top of the cap member. Alternatively, as shown in the embodiment of FIGS. 24 and 26, a zero is positioned adjacent a rectangular viewing window 334, preferably by permanent etching, to indicate a multiplication by ten of the indicia visible in the viewing window. One and two digit indicia 372 are formed on the top of the indicator member 360 such that a three digit number is indicated to the user.

Figure 3:
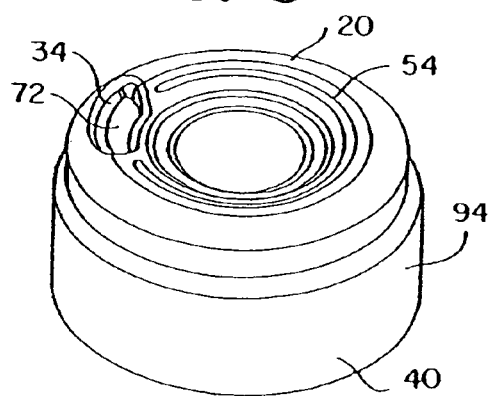
FIG. 3 is a top perspective view of the indicating device with the viewing window positioned in the top of the cap member.
Figure 3A:
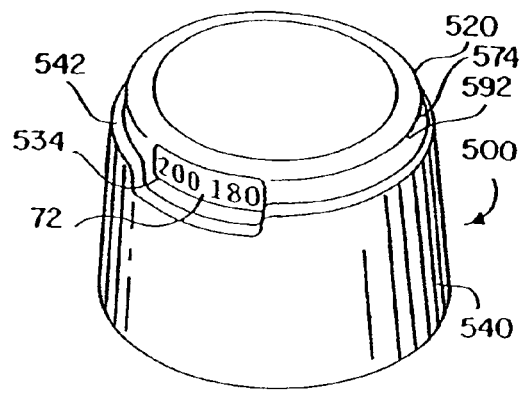
FIG. 3A is a top perspective view of the indicating device with the viewing window positioned along a side portion of the cap member.

In yet another alternative embodiment shown in FIG. 3A, the viewing window 534 is formed in an upper portion of the downwardly depending circumferential skirt 592 of the cap member. The indicia are applied to the outer circumferential surface of the indicator member skirt 574 so as to be visible through the window. In this embodiment, a rim 542 of the base member is preferably scalloped in alignment with the viewing window 534 to provide an unobstructed view of the indicia and to inform the user as to the location of the viewing window.

One of the skill in the art should understand that other indicia indicating the number of doses remaining in or dispensed from the container would include, but not be limited to, various alpha-numerical characters, words, terms or phrases (such as "full" and "empty"), scales, grids, arrows, raised portions, indentations, color coding and segmentation, shading and like markings, or any combination thereof. For example, a segmented color grid 172 displayed in the viewing window (as shown, e.g., in FIG. 1B) could turn from green, indicating a full container, to yellow, indicating an intermediate capacity, and finally to red, indicating an empty container. It should also be understood that the indicia can be formed integrally with the counter member, or applied thereto by means of paint, dye, etching, pad printing, hot stamping or adhesive labels. When using numerical indicia, the numbers can be arranged to go from 0 (or some beginning number) to the predetermined number of available doses such that a display of that number to the user indicates that the container is empty, or, conversely, to go from the starting predetermined number to 0 (or some ending number), which again indicates to the user that the container is empty.

In a preferred embodiment, the indicator member is made of acrylonitrile butadiene styrene ("ABS"), which is receptive to certain alternative processes of printing or applying the indicia, including pad printing and hot stamping. The cap member and base member are preferably made of a hard plastic material such as Acetel.

Referring to FIGS. 5-9 and 12-18, a drive mechanism is shown as including a drive assembly 80. The drive assembly includes a ratchet wheel 82 coaxially mounted to a drive member 86 on an axle 84. The ratchet wheel, drive member and axle can be made separately, with the ratchet wheel and drive member then mounted on the axle, or all three parts can be integrally molded as a one-piece component. The drive assembly is preferably made of hard plastic material such as Acetel.

Figure 42:
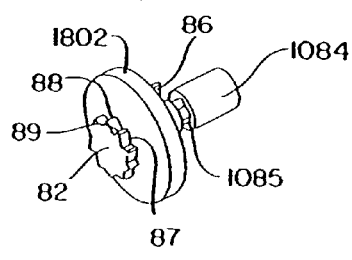
FIG. 42 is a perspective view of a drive assembly and dosage indicator member shown in FIG. 38.

In an alternative embodiment, shown in FIGS. 38 and 42, the drive assembly further includes a second dosage indicator member 1800 coaxially mounted with and between the drive member 86 and ratchet wheel 82. The indicator member 1800 is configured as a wheel and preferably includes dosage indicia positioned around the peripheral surface 1802 thereof. Preferably, the indicia are comprised of consecutive numerals running from 0 to 9.

In yet another alternative embodiment, shown in FIG. 44, the drive assembly includes a ratchet wheel 82 coaxially mounted with an indicator member 1800. The drive member 86 is formed separately from the ratchet wheel and indicator member and includes a single tooth 89 that is dimensioned to be received in a groove 1801 formed in a collar 1082 extending axially from the indicator member 1800. The tooth 89 of the drive member 86 is received in the groove 1801 of the collar and can be moved axially with respect to the collar, ratchet wheel and indicator member.

The ratchet wheel 82 includes a plurality of teeth 88 (preferably ten) formed around its periphery. Each of the teeth includes an engagement surface 89 and a tapered surface 87. As noted above, the drive member 86, whether integrally formed with the ratchet wheel or separately connected thereto, includes a single tooth 81, extending radially from the axle 84, or drive member collar.

In the embodiments shown in FIGS. 5, 6 and 45, the drive assembly is mounted to the cap member by engaging opposite ends of the axle 84 with downwardly extending hub portions 36, 236, 2236 such that the axle, ratchet wheel and drive member rotate about an axis substantially perpendicular to the axial movement of the cap member relative to the base member and to the axis of rotation of the indicator member. Alternatively, the drive assembly can be mounted to the base member in a similar manner.

Alternatively, as shown in the embodiment of FIGS. 38-39, the axle 84 is received in a single hub 1036, or flexible snap enclosure rib. In this embodiment, the drive assembly further includes a ramp 1083, which ramps up to a plurality of radially extending teeth 1085 formed around the rotational axis of the drive assembly. A larger diameter axle 1084 extends outwardly from the teeth. A reset member 1106 includes a grippable wheel portion 1107 and a collar 1109 that is dimensioned to be received in an laterally facing opening 1302 formed in the skirt of the cap member. A bearing support 1300 is formed around the periphery of the opening so as to provide support for the collar. The reset member 1106 further includes four flexible, resilient fingers 1304 extending axially from the collar 1109. Each finger 1304 includes an engagement portion 1306 extending radially inward from the end of the finger. The engagement portion is shaped to engage one of the teeth 1085 formed on the drive assembly. A protrusion 1308, or rib, is formed on one of the fingers so as to extend radially outward therefrom The protrusion 1308 acts as a drive portion and engages a downwardly depending protrusion 1310 formed on the bottom of the indicator member adjacent the gap 1061 formed between the teeth on the indicator member, as shown in FIG. 40 Preferably, the protrusion 1310 is positioned so as to be at the angular midpoint between the two teeth spanning the gap.

As shown in FIGS. 12-15, the drive mechanism further includes a pawl member 48, shown as a flexible rod or finger, which extends upwardly from the bottom portion of the base member and selectively engages one of the teeth of the ratchet wheel. Alternatively, the pawl member can be moveably secured to the cap member and extend through the base member to engage the top of the container, such that the axial movement of the cap member toward the container causes the pawl to move toward the ratchet wheel and engage one of the teeth thereon as described below. A non-return member 238, also shown as a flexible rod or finger, extends downwardly from the top portion of the cap member and selectively engages another of the teeth 88 of the ratchet wheel. It should be understood that the pawl member could alternatively extend from the cap member (and the non-return member from the base member) when the drive assembly is mounted to the base member, as described above.

In operation, as shown in FIGS. 12-21, the user depresses the cap 220 member from a fully extended position (see FIG. 12) toward the base member such that the cap member bottoms out in the base member at the bottom of the stroke (FIG. 14) and such that the base member imparts an axial load on the container until a metered dosage is dispensed therefrom. In a preferred embodiment, the biasing force of the spring 100 (shown in FIG. 6), or alternative return mechanism such as the resilient arm members which act as springs, is less than the biasing force of the spring located in the metering valve of the container, such that the cap member first bottoms out in the base member with the container then being moved downwardly in the housing until a metered dose is dispensed.

Referring to FIGS. 12, 13 and 14, as the cap member 220 is depressed toward the base member 40, the pawl 48 selectively engages the engagement surface 89 of one of the ratchet wheel teeth and rotates the ratchet wheel. The tapered surface 87 of one of the teeth formed on the ratchet wheel simultaneously biases the non-return member 238 outwardly until it selectively engages the next tooth near the bottom of the stroke. The user then releases the cap member whereinafter the spring 100 (shown in FIG. 6), or similar return mechanism, biases the cap member 220 away from the base member 40 until the engagement member engages the base portion at the top of the stroke as shown in FIG. 15. When the cap member is released by the user, the container is biased upwardly within the housing along the longitudinal axis such that the valve stem is moved to the closed position within the container. Simultaneously, as the cap member is released and allowed to move away from the base member, the pawl 48 is biased outwardly by the tapered surface 87 of one of the teeth on the ratchet wheel as the non-return member 238 prevents a backwards rotation thereof so as to maintain a unidirectional rotation of the ratchet wheel. At the top of the stroke (shown in FIG. 15), the pawl 48 is again placed in position for selective engagement with one of the teeth of the ratchet wheel. In this way, the ratchet wheel 82, and connected drive member 86 (shown in FIGS. 18-21), are advanced an incremental amount for every actuation of the container and the attendant release of medicament. The incremental amount is defined by and dependent on the number of teeth formed about the periphery of the ratchet wheel. When formed with ten teeth, as shown in the preferred embodiment, the ratchet wheel will make one full revolution for every ten actuations of the indicator device and container, or a tenth of a revolution for each actuation. One skilled in the art will appreciate that the ratchet wheel can be provided with various numbers of teeth formed about its periphery such that the more or less axial movements or actuations of the container are required to make one full rotation of the ratchet wheel.

Alternatively, the operation of the ratchet wheel can be reversed. In this embodiment, the pawl is biased outwardly by the tapered surface of one of the ratchet wheel teeth on the downstroke. At the bottom of the stroke, the pawl is biased into engagement with one of the teeth. When the cap member is released by the patient, the spring, or equivalent return mechanism, biases the cap member upwardly within the base member along the longitudinal axis such that the pawl member engages one of the teeth and thereby rotates the ratchet wheel an incremental amount. In this embodiment, the non-return member maintains the rotational position of the ratchet wheel on the downstroke.

As shown in FIGS. 18-20, 38 and 44 the drive member 86 is shown as preferably having a single tooth 81 or segment. Therefore, upon every tenth actuation, the drive member 86 is rotated such that the tooth selectively engages one of the teeth 266 formed on the indicator member so as to rotate the indicator member an incremental amount. The incremental amount of rotation is defined by the distance between adjacent teeth, otherwise defined as the circular pitch of the teeth. In this way, the drive member is selectively engaged with at least one of the teeth of the indicator member after and upon a predetermined number of axial movements of the cap member relative to the base member so as to rotate the indicator member the incremental amount. The predetermined number of axial movements required to cause the indicator member to rotate is defined by and dependent upon the reduction ratio of the ratchet wheel and drive member, which, in turn, is defined by dividing the number of teeth formed on the ratchet wheel by the number of teeth formed on the drive member. For example, as shown in the preferred embodiment, a ratchet wheel having ten teeth and a drive member having one tooth will result in an incremental movement of the indicator member, otherwise defined as the advancement of one tooth of the indicator member, upon every ten axial movements. Similarly, if the drive member had four teeth, and the ratchet wheel twenty, the predetermined number would equate to five axial movements, and so on. A one-to-one gear ratio would result in a predetermined number of one axial movement, wherein the indicator member would be moved upon every axial movement.

Figure 19:
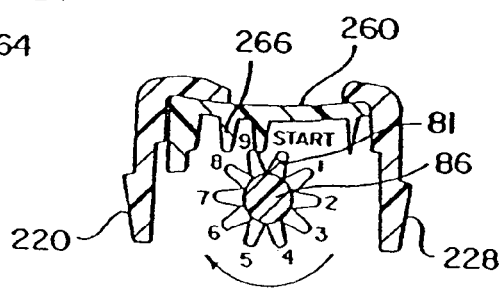
FIG. 19 is a cross-sectional view taken along line 19-19 of FIG. 18.
Figure 20:
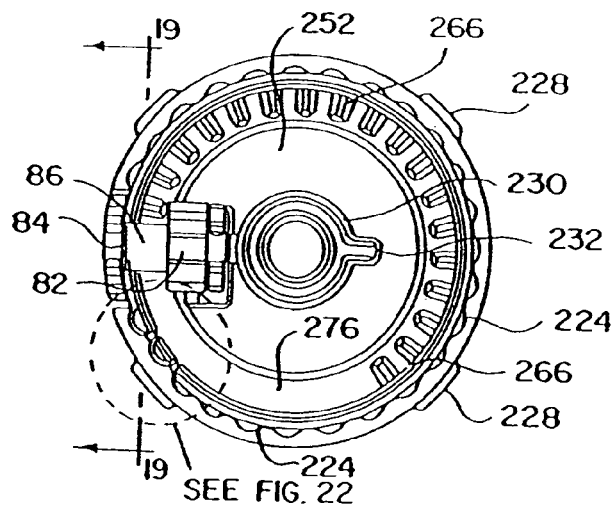
FIG. 20 is a bottom view of the assembly of FIG. 9 (without the spring) after the ratchet wheel and drive member have completed one revolution corresponding to a predetermined number of actuations.
Figure 21:
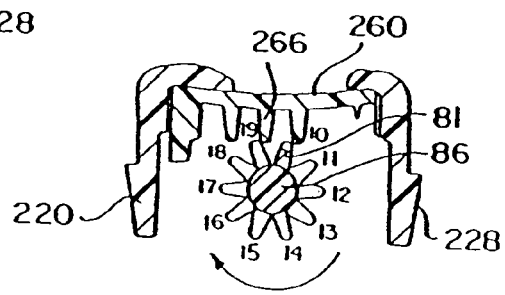
FIG. 21 is a cross-sectional view taken along line 21-21 of FIG. 20.
Figure 22:
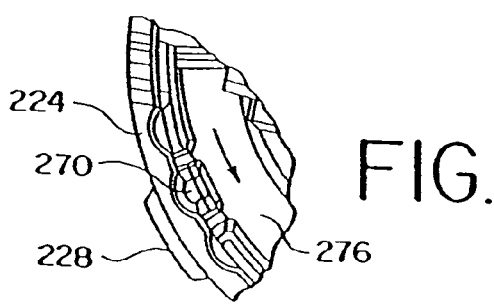
FIG. 22 is an enlarged partial bottom view of the cap member and indicator member showing the indicator member having an indexing member engaging an indentation formed on the cap member.

Referring to FIG. 19, the indicator member 260 and drive member 86 are shown prior to an initial actuation or use by the user. In particular, the drive member tooth is positioned adjacent the first tooth 266 on the indicator member. In this embodiment, wherein the ratchet wheel comprises ten teeth, ten actuations are required before the tooth 81 engages the first tooth 266 on the indicator member as shown in FIG. 21. At this point, the indicator has completed a single cycle equal to the number of predetermined number of axial movements, which results or culminates in the incremental movement of the indicator member. The cycle is then repeated (by again making the predetermined number of axial movements) so as to again culminate in the incremental movement of the indicator member. Preferably, as shown in FIGS. 1A, 3A, 24 and 26, numerical indicia (including numbers and dots) are applied in increments of ten to correlate to the preferred embodiment requiring ten axial movements for one incremental advancement of the indicator wheel.

The ratchet wheel and drive member with their reduction ratio provide a simple but reliable mechanism for advancing the indicator member. In particular, the indicator member can be made with fewer teeth than if it were required to advance upon every actuation of the indicator member and container. For ease of manufacturing, it is desirable to provide as coarse a pitch on each of the indicator member and ratchet wheel as possible, although the gears are still defined as fine-toothed gears. However, it is also intended that the indicator member make only a single revolution (single-cycle) corresponding to a complete evacuation of medicament from the container. Thus, when a large number of doses (on the order of 200 or more) are contained within the container, it is important for the ratchet wheel and drive member to provide a relatively high reduction ratio, such that 200 linear reciprocal movements of the cap member and container correspond to one or less revolutions of the indicator member. As such, the indicator member can be made with coarser teeth at less cost. In addition, larger coarser teeth interacting with a relatively large drive member tooth helps to improve the accuracy of the device as those parts mesh. In addition, the mechanism, and its attendant reduction ratio, permits the indicator member to make only a single revolution during the life of the container, i.e., until it is emptied, even when the container contains a relatively large number of metered doses (on the order of 200 or more doses). This single revolution corresponds to a usage cycle, which is defined as the movement of the dosage indicator from an initial reading, which indicates that the container is full, to a final reading, which indicates that the container is empty. Of course, the indicator member, if initially set to a smaller number of dosages, may make less than a complete revolution in completing a usage cycle.

In the alternative embodiments shown in FIGS. 38 and 44, the viewing window 1034, 2034 is large enough such that the first and second dosage indicator members 1060, 2060, 1800 with their indicia are visible therein. In the operation of these embodiments, the indicator member 1800 rotates with each actuation of the cap member 1020, 2020 relative to the base member 1040, 2040 as the ratchet wheel 82 is driven by the pawl member. The indicator member 1800 rotates about an axis substantially perpendicular to the axial movement of the cap member relative to the base member and to the rotational axis of the indicator member 1060, 2060. In the preferred embodiment, with the indicator member 1800 having "ones" indicia and the ratchet wheel 82 having ten teeth, the indicator member 1800 is advanced upon each actuation and provides indicia visible to the user to notify them of such advancement. As the indicator member 1800 completes a cycle, or rotation, the indicator member 1060, 2060 is advanced one increment by the drive member 86 and the indicator member 1800 begins another cycle. In this way, the user is advised as to each actuation of the indicating device and the attendant dispensment of a dosage from the attached container.

Where, as shown in FIGS. 5 and 40, the teeth 66, 1066 extend only partially around the periphery of the indicator member, the indicator member 60 1060 is not advanced after the drive member engages the last tooth, even when the cap member is repeatedly moved to actuate the container. This ensures that the indicator member cannot be advanced past the last indicia indicating that the container is empty to a first indicia indicating that the container is full, so as to confuse the user.

Figure 33:
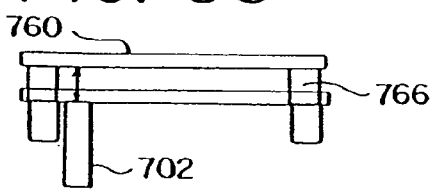
FIG. 33 is a side view of the indicator member and a lock member in a disengaged position.
Figure 35:
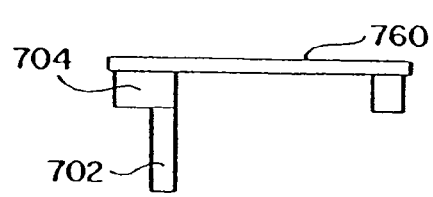
FIG. 35 is a side view of the indicator member and lock member in an engaged position.
Figure 34:
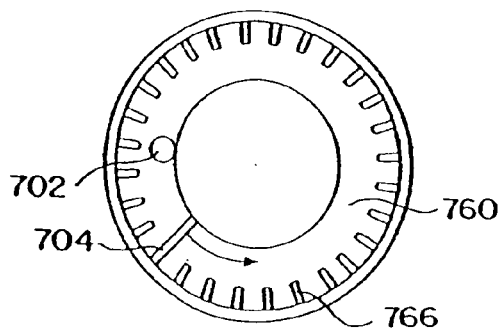
FIG. 34 is a bottom view of the indicator member and lock member shown in FIG. 33.
Figure 36:
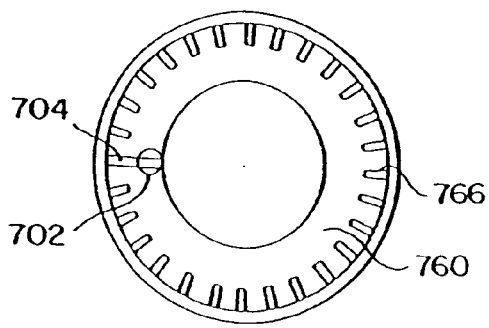
FIG. 36 is a bottom view of the indicator member and lock member shown in FIG. 35.

Alternatively, as shown in FIGS. 33-36, the indicating device includes a lock device. In particular, the base member includes a first lock member 702, configured as a post member extending upwardly from the bottom of the base member. The indicator member 760 includes a second lock member 704, shown in FIG. 35 as an extension of one of the plurality of teeth 766 formed around the circumference of the indicator member. In operation, the cap member is moved towards and away from the base member as described above so as to rotate the indicator member. During this operation, as shown in FIGS. 33 and 34, the first lock member 702 is positioned inside the inner diametrical surface of the plurality of teeth so as to not interfere therewith as it is moved into the recess formed by the indicator member as shown in FIG. 33. After the indicator member has made one complete rotation, which preferably correlates to an emptying of the container, the second lock member 704 is rotated over the first lock member 702 as shown in FIGS. 35 and 36. In this position, the cap member cannot be moved toward the base member and the user is thereby prevented from further discharging, or attempting to discharge, an empty container. The immobility of the cap member also provides a secondary indicia that the container is empty. One of skill in the art should understand that the size and shape of the first and second lock members can be varied. For example, a post member may extend from the cap member so as to engage a stepped surface in the base member.

Figure 29:
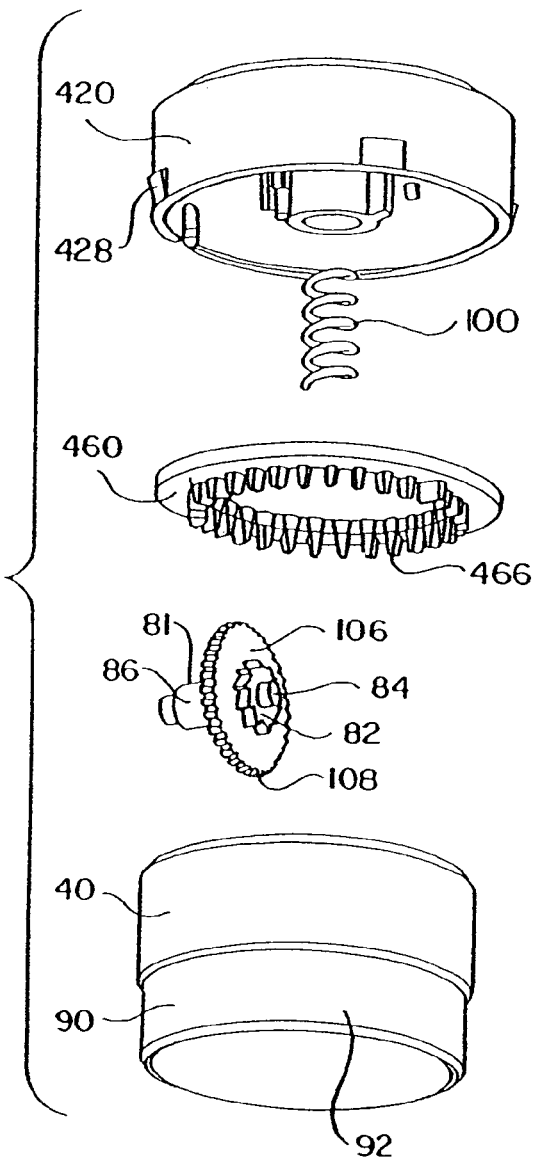
FIG. 29 is an exploded view of an alternative embodiment of the indicating device with an alternative embodiment of the reset device and an adapter.
Figure 30:
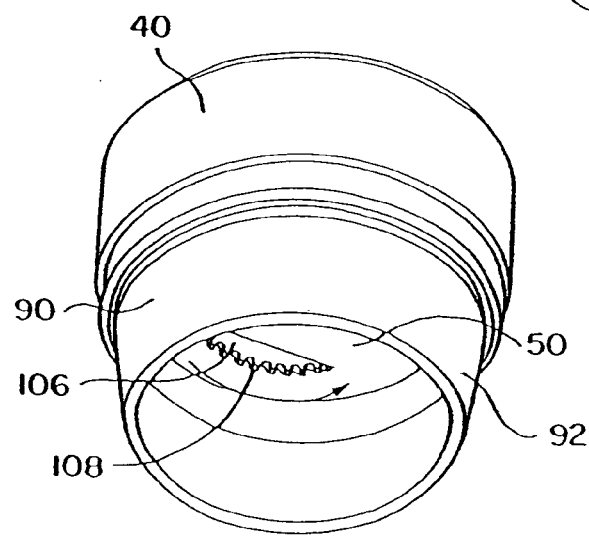
FIG. 30 is a bottom perspective view of the indicating device and adapter shown in FIG. 29.

As shown in FIGS. 29 and 30, a reset wheel 106 is coaxially mounted with the ratchet wheel 82 and drive member 86. The outer periphery 108 of the wheel, which includes a plurality of teeth for gripping by the user's thumb, is exposed as it extends through the bottom surface 50 of the base member. One of skill in the art should understand that the reset wheel can be exposed by extending from other portions of the indicator device for access by the user The user rotates the reset wheel 106 to manually rotate the indicator member to its original starting position, or any other desired setting, without having to move the cap member relative to the base member. In this way, the indicator member can be recycled for use on a new container, or can be moved to the proper setting prior to installing the indicating device on the container. In this way, the same indicating device can be used with various containers containing varying numbers of metered dosages of medicament. During the movement of the indicator wheel relative to the cap member, the force of the indexing member against the indentations in one of the cap member and indicator member is overcome such that the indexing member repeatedly moves into and out of engagement with the indentations as the indicator member is rotated by the user to the desired setting. This movement is similar to the movement of the indexing member occurring upon each incremental advancement of the indicator member relative to the cap member.

Preferably, the reset wheel of FIGS. 29 and 30 is used with an indicator member having teeth formed about its entire periphery, such that the indicator wheel need only be moved a few teeth (one or more) to return it to the zero (or full, e.g., 200) position. The reset wheel can be used with or without the lock device described above, since the wheel can be used to move or rotate the indicator wheel independent of any axial movement between the cap member and base member.

In an alternative embodiment shown in FIG. 28, a reset selector member 602 is mounted to the end of the axle and is exposed in an opening 604 in the side or skirt 694 of the base member. The reset selector member 602 is mounted on the axle. The selector member 602 is provided with a slot adapted to receive the head of a screw driver or like tool, which can be actuated by the user to rotate the axle, coaxially mounted drive member and indicator member until the desired indicia are visible in the viewing window. This feature can be valuable for resetting an indicating device for use on a new container, or for initially setting the device for the proper number of doses contained in the container. One of skill in the art should understand that recesses and/or protrusions other than the disclosed slot can be exposed on the selector member to allow the user to grip or otherwise operably engage the selector member and to thereafter rotate the indicator member. One of skill in the art should also understand that the opening in the base member could be positioned anywhere along the longitudinal path of the axle as the cap member moves relative to the base member so as to expose the selector member when aligned with the opening.

In yet another alternative embodiment, shown in FIG. 27, a selector window 806 is formed in the top of the cap member. A reset selector member 802, configured as a protrusion or like grippable member, is exposed in the window as the indicator member is rotated to the empty position. In one embodiment, as described above, the plurality of teeth are formed only around a portion of the periphery of the indicator member so as to leave a gap between the first and last tooth. In such an embodiment, the selector window 806 is preferably of such length that the user can move the reset selector member 802 within the window until the first tooth is again in position for engagement with the drive member. It should be understood, however, that the reset selector member can also be used with an indicator member having teeth formed around the entire periphery of the member.

In an alternative embodiment, a plurality of reset members, or a similar grippable surface, configured for example as a plurality of notches or teeth, can be formed around the entire periphery of the indicator member and exposed in a selector window, or alternatively, in the viewing window. In such an embodiment, the indicator wheel can be rotated to expose different indicia at any time simply by engaging the reset selector members on the indicator member with the user's thumb or like member.

In yet another embodiment, shown in FIG. 24, an opening, or selector window 906, is provided in the top of the cap member. A thin tool, such as a paper clip, is inserted through the opening to bias the resilient indexing member 370 out of engagement with the indicator member. The user can then operably engage the indicator member with their finger or the like, either through the viewing window or a selector window, to move the indicator member to the desired setting.

Figure 43:
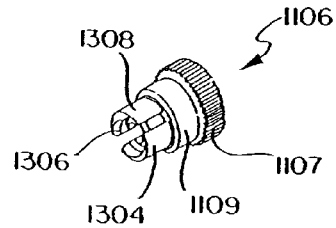
FIG. 43 is a perspective view of the reset member shown in the indicating device shown in FIG. 38.

In yet another alternative embodiment, shown in FIG. 43, the reset member, with the collar 1109 disposed on the axle 1084 of the drive assembly, is pulled axially outward with respect thereto from a disengaged position, where the engagement portions 1306 of the flexible fingers 1304 are positioned circumferentially around the axle 84, to an engaged reset position, such that the engagement portions 1306 of the flexible fingers are biased outwardly as they ride up the ramp 1083 and are thereafter moved into engagement with the teeth 1085 formed around the axle of the drive assembly. The user then rotates the reset member 1106 about a rotation axis, which is substantially perpendicular to the axial movement of the cap member relative to the base member. As the reset member is rotated, the protrusion 1308 on the flexible fingers is brought into engagement with the protrusion 1310 on the indicator member 1060 so as to rotate the indicator member an incremental amount and thereby bring the first tooth on the other side of the gap 1061 into position for engagement by the drive member, thus bridging the gap 1061 between the teeth of the indicator member. As the reset member 1106 is further rotated, the drive member tooth 89 engages the teeth 1066 of the indicator member, and the reset member can be rotated to manually drive the indicator member, or indicator members, to the desired preset condition. For example, the indicator members can be reset to indicate 200 dosages for use with a container having 200 dosages.

In a preferred embodiment, the engagement portions 1306 and/or teeth 1085 formed on the axle of the drive assembly are configured to allow rotation of the drive member in only one direction. Therefore, rotation of the reset wheel in an opposite direction will not effect a rotation of the drive member in that same direction as the flexible fingers, with their engagement portions, will simply slide over the teeth formed about the axle. This one-way rotation prevents the drive member from engaging and rotating the indicator member in an opposite direction, which direction is opposed both by the non-return member engaging the ratchet wheel, and the one-way indexing interface between the cap member and indicator member.

To install the reset member and drive assembly, the drive assembly is installed in a vertical manner such that the axle 84 is received in the flexible snap enclosure 1036. Once the drive assembly is snapped in place, the reset member 1106 is inserted through the opening in the cap member and over the axle 1084 until the fingers eventually are disposed around the axle 84 in the disengaged position. In this way, the reset member, which is supported by the bearing surface 1300 of the cap member, further supports the drive assembly.

In yet another embodiment, best shown in FIGS. 52-55, the indicator member 2060 has a plurality of teeth extending around the entire circumference thereof. At least one of the teeth 2067 has a cut-away portion 2069 aligned with the tooth 89 of the drive member. Accordingly, at the end of a cycle, the drive member is positioned in a disengaged position where even repetitive actuations of the indicating device do not lead to the advancement of the indicator member as the drive member, with its one or more teeth 89, merely passes through the cut-away portion 2069 of the tooth, with which it is aligned. In this embodiment, however, the drive member 86 is axially moveable with respect to the indicator member 1800 and ratchet wheel 82.

As best shown in FIGS. 44, 47 and 52-56, a reset member 2106 includes a grippable wheel 2107 connected to a drive shaft 2109. As shown in the preferred embodiment of FIG. 47, the end of the drive shaft includes a plurality of teeth 2306, that engage slots 2308 or openings dimensioned to receive the teeth formed in one end of the drive member 86. The drive member is installed on the shaft of the reset wheel such that the teeth 2306 formed on the end thereof engage the slots 2308 formed in the drive member. The drive member is then inserted into the groove 1801 of the collar 1082 extending from the indicator member.

In operation, the user pulls the reset member 1206 axially outward so as to move axially the drive member 86 from a disengaged position, where the drive member tooth 89, or teeth, is aligned with the cut-away portion 2069 of the tooth on the indicator member, to an engaged or reset position, where the drive member tooth is brought into engagement with the portion 2067 of the tooth that is not cut-away. In the reset position, the user rotates the reset wheel 2107 and connected drive member 86 so as to advance the indicator member 2060, or indicator members, to the desired setting independent of the axial movement of the cap member relative to the base member. In the disengaged position, the reset wheel is recessed between a pair of tapered flanges formed around the circumference of the base member.

As shown in FIGS. 44 and 52-56, the indicator member 2060 includes a cover portion 2087 that extends radially inward from the top portion of the indicator member. The cover portion is brought into alignment with the viewing window at the end of the usage cycle such that the indicator 1800, which can continue to be spun beneath the cover portion is not visible. Indicia, such as the number "0" or the words "end" or "empty" can be applied to the cover portion to inform the user that the container is empty.

As shown in FIGS. 37-43, the indicating device also includes a usage indicator member 1500. The indicator member 1500 is configured as a ring and is disposed around the skirt 1074 of the dosage indicator member 1060 where it is trapped between the rim flange 1078 of the indicator member and the bottom surface of the top of the cap member. In this way, the usage indicator member 1500 is supported by and is moveable about the dosage indicator member 1060. The indicator member 1500 also is thereby rotatably mounted about an axis substantially parallel to the axial movement of the cap member relative to the base member. The indicator member 1500, which is configured as a ring, has a plurality of teeth 1502 formed around the outwardly facing radial periphery thereof. As the indicator member 1060 is advanced as explained above, a flexible finger 1273 formed along the circumferential rim 1078 of the indicator member 1060 is biased radially inward by a ramp 1277 formed on the inside of the cap member so as to engage at least one of the plurality of teeth 1502 formed on the indicator member and thereby advance the indicator member an incremental amount, defined by the distance between adjacent teeth. The number of teeth formed around the indicator member corresponds to the number of intended usage cycles of the indicating device.

In the preferred embodiment, which has only a single ramp 1277, the usage indicator member 1500 is advanced one tooth upon each complete rotation of the dosage indicator member 1060, which corresponds to one complete usage cycle for the indicating device. For example, the indicating device can be initially set to reveal an initial count of 200 dosages. As the indicating device is successively actuated to dispense the dosages, the indicator members 1060, 1800, with indicia, are actuated to count down until they reveal a final count of 0 dosages available for use. At that time, the drive assembly is positioned in the disengaged position, as explained above.

As the reset member 1106 is used to actuate the drive assembly to reset the device for another usage cycle, the indicator member 1060 with its resilient finger 1273 is biased into engagement by the ramp 1277 such that the usage indicator member is rotated. In this way, the indicator member 1500 is rotated, or advanced, upon the completion of each successive usage cycle. The number of teeth 1502 on the indicator member 1500 corresponds to the number of intended uses for the indicator. For example, in the embodiment shown in FIGS. 38 and 41, the indicator member 1500 has twelve teeth corresponding to an intended twelve uses of the indicating device with twelve different containers. As noted above, the reset member can be used to reset the indicia at any desired reading, such that one indicating device can be used with successive containers having different numbers of dosages contained therein. The indicator member 1500 also includes a stop member 1506 formed as a protrusion that extends radially inward from the top of the indicator member. The stop member 1506 engages a stop member (not shown) extending downwardly from the top portion of the cap member upon completion of the final predetermined usage cycle. This engagement prevents the user from attempting to advance the dosage indicator member 1060 by way of the reset member and drive assembly, because the finger 1273 is biased into engagement with at least one of the teeth on the usage indicator member, which is immobilized. In this way, the entire device is immobilized. It should be understood that although the preferred embodiment is configured for twelve usage cycles, the usage indicator member could be provided with more or less teeth corresponding to more or less total available usage cycles.

Figure 41:
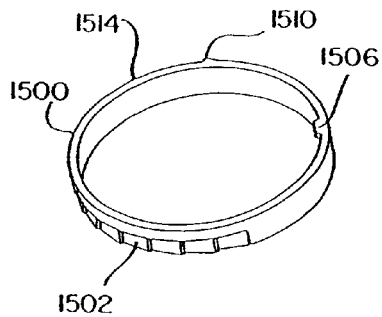
FIG. 41 is a top perspective view of a usage indicator member shown in FIG. 38.

Referring to FIG. 41, the usage indicator member 1500 further includes an indexing member 1510 configured as a protrusion extending radially outward from the outer circumferential surface of the indicator member. The indexing member 1510 selectively engages a plurality of teeth 1512 formed around the inner circumferential surface of the skirt of the cap member. The indexing member 1510 and teeth 1512 are configured as a ratchet to allow one-way rotation of the indicator member 1500 relative to the cap member 1020. In a preferred embodiment, the indexing member and teeth are tapered to interact and provide for the one-way action.

Figure 37:
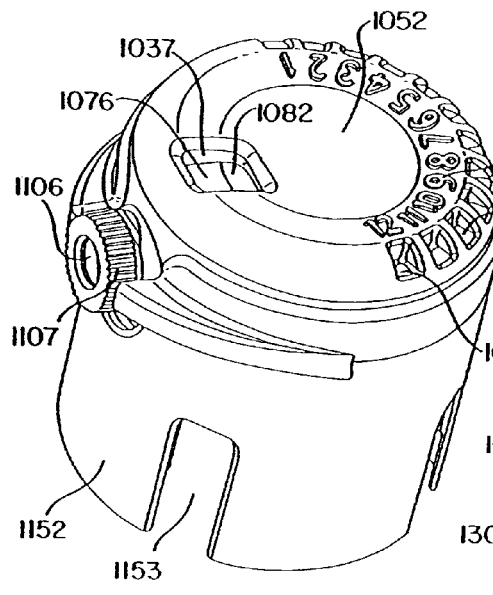
FIG. 37 is a perspective view of an alternative embodiment of an indicating device having at least one indicator member with dosage indicia and an indicator member with usage indicia.

As shown in FIGS. 37 and 38, a plurality of viewing windows 1600 are arranged around the outer periphery of the top of the cap member. A plurality of indicia 1602, shown as successive numbers, are affixed to the top of the cap member adjacent the viewing windows. The upper edge 1514 of the usage indicator member is provided with indicia that is visible through the viewing windows 1600, such that the user can ascertain which usage cycle the indicating device is currently functioning in. For example, in the embodiment shown in FIGS. 37 and 38, twelve viewing windows 1600 are provided with the numbers 1 to 12 arranged adjacent thereto, which correspond to the 12 usage cycles defining the life of the indicating device. The numbers, or other indicia such as various colors, can be applied to the cap member by printing, molding or any other of the techniques described above. Alternatively, a single viewing window can be provided to expose the indicator member, whereupon indicia can be applied to the top surface or upper edge 1514 thereof, or, if the window is provided in the side of the cap member, along the outer circumferential surface thereof.

In the embodiment shown in FIGS. 44-45 and 49-51, the usage indicator member 2500 includes a hub 2520 having an opening 2521 that is rotatably mounted on a post 2522 extending downwardly from the inner surface of the top portion of the cap member 2020. In this way, the usage indicator member 2500 is rotatably mounted to the cap member 2020 about an axis substantially parallel to and spaced from the rotational axis of the dosage indicator member 2060. The axis of rotation for the dosage usage indicator member is also substantially parallel to the axial movement of the cap member relative to the base member.

The indicator member 2500 includes a ring 2524 formed about the hub 2520 which is connected thereto with a rib 2526 and a bottom surface 2528. The indicator member 2500 has a plurality of inwardly, radially extending teeth 2514 formed about the inner periphery of the ring, and a plurality of outwardly, radially extending teeth 2502 formed on the bottom surface of the indicator member around the outer periphery thereof. Both pluralities of teeth are configured as ratchet teeth to allow only for one-way rotation of the indicator member 2500.

Referring to FIG. 46, an engagement member 2573 extends from the indicator member 2060 and engages an engagement surface of one of the ratchet teeth 2502 as the dosage indicator member 2060 completes one full cycle. As the engagement member 2573 engages the engagement surface of one of the teeth 2502, the indicator member is rotated an incremental amount.

Figure 51:
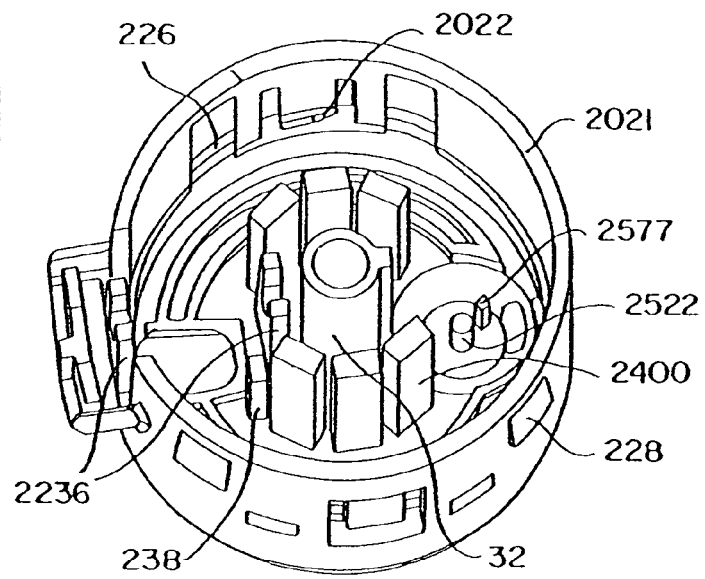
FIG. 51 is a bottom perspective view of the cap member shown in FIG. 44.
Figure 52:
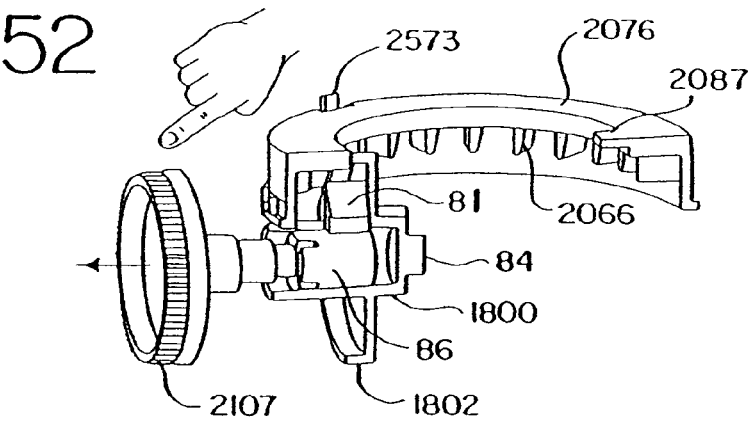
FIG. 52 is a cut-away perspective view of the reset member shown in FIG. 44 with the drive member in a disengaged position.
Figure 53:
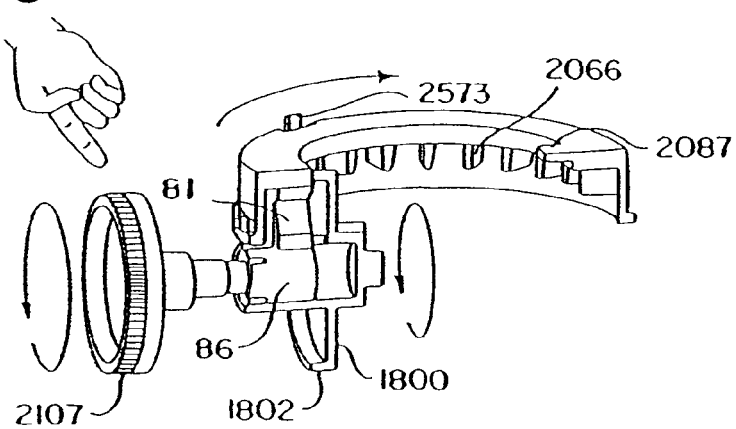
FIG. 53 is a cut-away perspective view of the reset member shown in FIG. 44 with the drive member in the engaged reset position.

Referring to FIG. 51, an indexing member 2577 extends downwardly from the cap member 2020 in a parallel and spaced apart relationship with the post 2522. The indexing member 2577 is disposed in the space between the hub 2520 and the ring 2524 and selectively engages the inner teeth 2514 formed around the inner periphery of the ring. Again, the indexing member 2577 and teeth 2514 are preferably configured to allow for only one-way rotation of the usage indicator member 2500 relative to the cap member 2020. The number and angular spacing between the inner and outer teeth 2514, 2502 correspond such that the advancement of the indicator member 2500 by way of engagement of the engagement member 2573 with one of the outer 2502 teeth further advances the indexing member 2577 one tooth 2514 along the inner periphery of the ring. The predetermined number of usages for the indicating device corresponds to the number of teeth formed around the inner periphery of the ring After the completion of the final usage cycle, the indexing member 2577 is brought into engagement with the rib 2526, which functions as a stop member and does not permit the indicator member to be further rotated or advanced. At the same time, the engagement member 2573 is brought into engagement with one of the teeth 2502 formed about the outer periphery of the ring such that the indicator member also cannot be advanced. In this way, the device is immobilized. Again, the indicating device can be provided with a predetermined number of inner and outer teeth, which corresponds to the number of predetermined usage cycles for the indicating device.

The upper surface 2528 of the indicator member ring, which is preferably domed, is provided with usage indicia to indicate the number of usage cycles completed or remaining for the indicating device. The usage indicia is visible to the user through a viewing window 2600 provided in the cap member, as shown in FIG. 44. Again, the usage indicia can take the form of various alphanumeric characters, colors or any of the other varieties described above.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is

1. A dispenser having an indicating device suitable for indicating the number of metered dosages that have been dispensed from or remain in a container, the dispenser comprising:

a container having a bottom, a top and a valve stem extending from said top;

a dispenser housing connected to said valve stem;

an indicator housing having a lower portion connected to said bottom of said container in a non-rotatable relationship, and an upper portion having an outer surface visible to a user, wherein static numerical indicia are applied to said outer surface in a non-rotatable relationship relative to said container; and an indicator member moveably mounted in said indicator housing, wherein said indicator member is moveable relative to said numerical indicia, wherein said container is moveable relative to said dispenser housing along a longitudinal axis defined by said valve stem, and wherein said indicator member is rotatable about said longitudinal axis.

2. The dispenser of claim 1 wherein said numerical indicia are arranged in an at least a partially circumferential pattern around a top of said upper portion.

3. The dispenser of claim 2 wherein said upper portion comprises at least one viewing window positioned proximate said numerical indicia, wherein said indicator member is visible to the user through said viewing window.

4. The dispenser of claim 3 wherein said at least one viewing window provides an arcuate shaped viewing arrangement radially displaced from said circumferential pattern of numerical indicia.

5. The dispenser of claim 3 wherein said circumferential pattern of numerical indicia extends less than 360 degrees around said outer surface of said upper portion.

6. The dispenser of claim 1 wherein said housing comprises a substantially cylindrical sidewall and a top wall defining said outer surface.

7. The dispenser of claim 6 wherein said sidewall surrounds and engages said container.

8. The dispenser of claim 1 wherein said indicator member comprises an indicator directed to said numerical indicia.

9. An indicating device suitable for indicating the number of metered dosages that have been dispensed from or remain in a container, said indicating device comprising:
a base member;
a cap member moveably connected to said base member, said cap member moveable relative to said base member along an axial path between at least a first and second position;
a resilient cantilevered member extending from one of said base member and said cap member; and
a biasing surface formed on the other of said base member and said cap member, wherein at least a portion of said resilient cantilevered member engages and is moveable along said biasing surface in a first direction as said cap member is moved from said first position to said second position, wherein said biasing surface biases said resilient cantilevered member to a flexed condition as said cap member is moved relative to said base member from said first position to said second position, and wherein said at least said portion of said resilient cantilevered member engages and is moveable along said biasing surface in a second direction opposite said first direction as said cap member is moved from said second position to said first position.

10. The indicating device of claim 9 wherein said cap member is moved towards said base member along said axial path as said cap member is moved between said first and second positions.

11. The indicating device of claim 9 wherein said resilient cantilevered member extends from said cap member and said biasing surface is formed on said base member.

12. The indicating device of claim 9 wherein said resilient cantilevered member extends in the direction of the axial movement of said cap member relative to said base member.

13. The indicating device of claim 12 wherein said biasing surface biases said at least said portion of said resilient cantilevered member in a flexed direction that is substantially perpendicular to the direction of the axial movement as said cap member is moved relative to said base member from said first position to said second position.

14. The indicating device of claim 9 wherein said at least said portion of said resilient cantilevered member comprises an end portion thereof.

15. The indicating device of claim 9 wherein said biasing surface comprises a ramped surface that slopes away from said end portion of said resilient cantilevered member when said cap member is in said first position.

16. The indicating device of claim 9 wherein said base member has a cylindrical wall that is adapted to surround at least a portion of the container.

17. The indicating device of claim 9 further comprising an indicator member rotatably mounted to one of said cap member and said base member.

18. The indicating device of claim 17 wherein said indicator member is rotatably mounted to said cap member.

19. The indicating device of claim 1 wherein said upper and lower portions are moveable relative to each other along said longitudinal axis.

20. A dispenser having an indicating device suitable for indicating the number of metered dosages that have been dispensed from or remain in a container, the dispenser comprising:
a container having a bottom, a top and a valve stem extending from said top;
a dispenser housing connected to said valve stem;
an indicator housing connected to said bottom of said container and having an upper surface visible to a user, wherein said indicator housing is moveable with said container relative to said dispenser housing along a longitudinal axis, and wherein static numerical indicia are applied to said upper surface and are non-rotatable relative to said longitudinal axis; and
an indicator member rotatably mounted in said indicator housing about said longitudinal axis, wherein said indicator member is rotatable about said longitudinal axis relative to said static numerical indicia.

21. The dispenser of claim 20 wherein said numerical indicia are arranged in an at least a partially circumferential pattern around said upper surface.

22. The dispenser of claim 21 wherein said upper surface comprises at least one viewing window positioned proximate said numerical indicia, wherein said indicator member is visible to the user through said viewing window.

23. The dispenser of claim 22 wherein said at least one viewing window provides an arcuate shaped viewing arrangement radially displaced from said circumferential pattern of numerical indicia.

24. dispenser of claim 20 wherein said indicator member comprises an indicator directed to said numerical indicia.

25. The dispenser of claim 20 wherein said numerical indicia are arranged substantially within a plane formed substantially perpendicular to said longitudinal axis.

* * * * *